US008350010B2

(12) United States Patent
Chuntharapai et al.

(10) Patent No.: US 8,350,010 B2
(45) Date of Patent: Jan. 8, 2013

(54) ANTI-ALPHA5/BETA1 ANTIBODY

(75) Inventors: Anan Chuntharapai, Colma, CA (US); Gregory D. Plowman, San Carlos, CA (US); Marc Tessier-Lavigne, Woodside, CA (US); Yan Wu, Foster City, CA (US); Weilan Ye, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/171,289

(22) Filed: Jun. 28, 2011

(65) Prior Publication Data

US 2012/0195908 A1 Aug. 2, 2012

Related U.S. Application Data

(63) Continuation of application No. 12/293,382, filed as application No. PCT/US2007/064572 on Mar. 21, 2007, now abandoned.

(60) Provisional application No. 60/784,704, filed on Mar. 21, 2006, provisional application No. 60/785,330, filed on Mar. 22, 2006, provisional application No. 60/871,743, filed on Dec. 22, 2006.

(51) Int. Cl.
*C07K 16/18* (2006.01)
(52) U.S. Cl. .................................................. 530/388.1
(58) Field of Classification Search ........................ None
See application file for complete search history.

(56) References Cited

U.S. PATENT DOCUMENTS

| | | | |
|---|---|---|---|
| 5,540,933 A | 7/1996 | Ruoslahti et al. | |
| 5,583,203 A | 12/1996 | Hemler et al. | |
| 5,627,263 A | 5/1997 | Ruoslahti et al. | |
| 5,766,857 A | 6/1998 | Ruoslahti et al. | |
| 5,981,478 A | 11/1999 | Ruoslahti et al. | |
| 5,985,278 A | 11/1999 | Mitjans et al. | |
| 6,242,577 B1 | 6/2001 | Ruoslahti et al. | |
| 6,852,318 B1 | 2/2005 | Varner | |
| 7,056,506 B2 | 6/2006 | Varner | |
| 7,067,619 B2 | 6/2006 | Ruoslahti et al. | |
| 7,189,507 B2 | 3/2007 | Mack et al. | |
| 7,276,589 B2 | 10/2007 | Ramakrishnan et al. | |
| 7,285,268 B2 | 10/2007 | Ramakrishnan et al. | |
| 7,311,911 B2 | 12/2007 | Varner | |
| 7,435,589 B2 | 10/2008 | Mack et al. | |
| 7,662,384 B2 | 2/2010 | Ramakrishnan et al. | |
| 2002/0015970 A1 | 2/2002 | Murray et al. | |
| 2002/0019330 A1 | 2/2002 | Murray et al. | |
| 2003/0124579 A1 | 7/2003 | Mack et al. | |
| 2003/0152926 A1 | 8/2003 | Murray et al. | |
| 2003/0232350 A1 | 12/2003 | Afar et al. | |
| 2004/0009494 A1 | 1/2004 | Murray et al. | |
| 2004/0033495 A1 | 2/2004 | Murray et al. | |
| 2004/0076955 A1 | 4/2004 | Mack et al. | |
| 2004/0253606 A1 | 12/2004 | Aziz et al. | |
| 2004/0259152 A1 | 12/2004 | Murray et al. | |
| 2005/0002930 A1 | 1/2005 | Johnson et al. | |
| 2005/0163768 A1 | 7/2005 | Eckert et al. | |
| 2005/0163769 A1 | 7/2005 | Ramakrishnan et al. | |
| 2005/0260210 A1 | 11/2005 | Ramakrishnan et al. | |
| 2006/0008415 A1 | 1/2006 | Kaisheva et al. | |
| 2006/0127407 A1 | 6/2006 | Chen et al. | |
| 2006/0241067 A1 | 10/2006 | Varner et al. | |
| 2007/0042360 A1 | 2/2007 | Afar et al. | |
| 2007/0059748 A1 | 3/2007 | Afar et al. | |
| 2007/0161016 A1 | 7/2007 | Afar et al. | |
| 2008/0026033 A1 | 1/2008 | Ramakrishnan | |
| 2008/0026458 A1 | 1/2008 | Ramakrishnan | |
| 2008/0113898 A1 | 5/2008 | Varner | |
| 2008/0188641 A1 | 8/2008 | Varner | |
| 2008/0233108 A1 | 9/2008 | Varner | |
| 2008/0260732 A1 | 10/2008 | Ramakrishnan | |
| 2009/0041785 A1 | 2/2009 | Johnson et al. | |
| 2009/0081207 A1 | 3/2009 | Menrad et al. | |
| 2009/0111828 A1 | 4/2009 | Kettle | |
| 2009/0137601 A1 | 5/2009 | Barry et al. | |
| 2009/0220504 A1 | 9/2009 | Chuntharapai et al. | |

FOREIGN PATENT DOCUMENTS

| | | |
|---|---|---|
| EP | 1 049 718 B1 | 11/2000 |
| EP | 1 075 277 B1 | 2/2001 |
| WO | WO-95/14714 A1 | 6/1995 |
| WO | WO-99/37683 A1 | 7/1999 |
| WO | WO-99/58139 A2 | 11/1999 |
| WO | WO-99/58139 A3 | 11/1999 |
| WO | WO-00/64480 A1 | 11/2000 |
| WO | WO-01/11086 A2 | 2/2001 |
| WO | WO-01/11086 A3 | 2/2001 |
| WO | WO-01/11086 C1 | 2/2001 |
| WO | WO-02/079492 A2 | 10/2002 |
| WO | WO-02/079492 C1 | 10/2002 |
| WO | WO-02/086443 A2 | 10/2002 |
| WO | WO-02/086443 C1 | 10/2002 |

(Continued)

OTHER PUBLICATIONS

Akiyama, S.K. et al. (Aug. 1989). "Analysis of Fibronectin Receptor Function With Monoclonal Antibodies: Roles in Cell Adhesion, Migration, Matrix Assembly, and Cytoskeletal Organization," *The Journal of Cell Biology* 109:863-875.

(Continued)

*Primary Examiner* — Michael Pak

(74) *Attorney, Agent, or Firm* — Morrison & Foerster LLP

(57) ABSTRACT

The present invention relates to the use of VEGF antagonists and alpha5beta1 antagonists for treating cancer and inhibiting angiogenesis and/or vascular permeability, including inhibiting abnormal angiogenesis in diseases. The present invention also relates to use of a VEGFR agonists and alpha5beta1 agonists to promote angiogenesis and vascular permeability. The present invention also relates to new anti-alpha5beta1 antibodies, compositions and kits comprising them and methods of making and using them.

22 Claims, 14 Drawing Sheets

FOREIGN PATENT DOCUMENTS

| | | |
|---|---|---|
| WO | WO-02/098358 A2 | 12/2002 |
| WO | WO-02/098358 A3 | 12/2002 |
| WO | WO-02/102235 A2 | 12/2002 |
| WO | WO-02/102235 A3 | 12/2002 |
| WO | WO-03/003906 A2 | 1/2003 |
| WO | WO-03/003906 A3 | 1/2003 |
| WO | WO-03/025138 A2 | 3/2003 |
| WO | WO-03/025138 A3 | 3/2003 |
| WO | WO-03/042661 A2 | 5/2003 |
| WO | WO-03/042661 A3 | 5/2003 |
| WO | WO-04/001384 A2 | 12/2003 |
| WO | WO-04/001384 A3 | 12/2003 |
| WO | WO-2004/048938 A2 | 6/2004 |
| WO | WO-2004/048938 A3 | 6/2004 |
| WO | WO-2004/056308 A2 | 7/2004 |
| WO | WO-2004/056308 A3 | 7/2004 |
| WO | WO-2004/089988 A2 | 10/2004 |
| WO | WO-2004/089988 A3 | 10/2004 |
| WO | WO-2005/092073 A2 | 10/2005 |
| WO | WO-2005/092073 A3 | 10/2005 |
| WO | WO-2006/004736 A2 | 1/2006 |
| WO | WO-2006/004736 A3 | 1/2006 |
| WO | WO-2007/060408 A2 | 5/2007 |
| WO | WO-2007/060408 A3 | 5/2007 |
| WO | WO-2007/060409 A1 | 5/2007 |
| WO | WO-2007/091046 A1 | 8/2007 |
| WO | WO-2007/134876 A2 | 11/2007 |
| WO | WO-2007/134876 A3 | 11/2007 |
| WO | WO-2007/134876 A8 | 11/2007 |
| WO | WO-2007/134876 C1 | 11/2007 |
| WO | WO-2007/134876 C2 | 11/2007 |

OTHER PUBLICATIONS

Akiyama, S.K. et al. (1995). "Fibronectin and Integrins in Invasion and Metastasis," *Cancer and Metastasis Reviews* 14:173-189.

Baluk, P. et al. (2005, e-pub. Dec. 24, 2004). "Cellular Abnormalities of Blood Vessels as Targets in Cancer," *Current Opinion in Genetics & Development* 15:102-111.

Bauer, J.S. (1993). "The Functional Role of Integrins in Cell Adhesion, Motility and Differentiation (Integrins, Extracellular Matrix)," *Dissertation Abstracts International* 54/06-B:3009, one page.

BD Biosciences. (Oct. 26, 2004). "Purified Mouse Anti-Human Monoclonal Antibody" BD Pharmingen™ Technical Data Sheet, located at <www.bdbiosciences.com <http://www.bdbiosciences.com>, three pages.

Bliss, R.D. et al. (Feb. 24, 1995). "The Role of β1 Integrins in Adhesion of Two Breast Carcinoma Cell lines to a Model Endothelium," *Clinical & Experimental Metastasis* 13(3):173-183.

Burrows, L. et al. (Dec. 1, 1999). "Fine Mapping of Inhibitory Anti-α5 Monoclonal Antibody Epitopes That Differentially Affect Integrin-Ligand Binding," *The Biochemical Journal* 344(2):527-533.

Chunmeng, S. et al. (Sep. 2004). "Effects of Dermal Multipotent Cell Transplantation on Skin Wound Healing," *The Journal of Surgical Research* 121(1):13-19.

Cobleigh, M.A. et al. (Oct. 2003). "A Phase I/II Dose-Escalation Trial of Bevacizumab in Previously Treated Metastatic Breast Cancer," *Semin Oncol* 30(5)(Supp. 16):117-124.

Collo, G. et al. (Jan. 25, 1999). "Endothelial Cell Integrin α5 β1 Expression is Modulated by Cytokines and During Migration in Vitro," *Journal of Cell Science* 112:569-578.

Danen, E.H.J. et al. (1994). "Emergence of α5 β1 Fibronectin- and αv β3 Vitronectin-Receptor Expression in Melanocytic Tumor Progression," *Hisopthology* 24:249-256.

Davies, J. et al. (1996). "Affinity Improvement of Single Antibody VH Domains: Residues in all Three Hypervariable Regions Affect Antigen Binding," *Immunotechnology* 2(3):169-179.

Du Manior et al. (Feb. 1, 2006). "Strategies for Delaying or Treating in Vivo Acquired Resistance to Trastuzumab in Human Breast Cancer Xenografts," *Clinical Cancer Research, The American Association for Cancer Research* 12(3):904-916.

Economopoulou, M. et al. (Dec. 1, 2005). "Inhibition of Pathologic Retinal Neovascularization by α-Defensins," *Blood* 106(12):3831-3838.

Eming, S.A. et al. (2007). "Regulation of Angiogenesis: Wound Healing as a Model," *Progress in Histochemistry and Cytochemistry* 42:115-170.

Ferrara, N. (2005, e-pub. Nov. 21, 2005). "VEGF as a Therapeutic Target in Cancer," *Oncology* 69(Suppl. 3):11-16.

Ferrara, N. et al. (Dec. 15, 2005). "Angiogenesis as a Therapeutic Target," *Nature* 438(7070):967-974.

Fogerty, F.J. et al. (Aug. 1990). "Inhibition of Binding of Fibronectin to Matrix Assembly Sites by Anti-Integrin (α5 β1) Antibodies," *The Journal of Cell Biology* 111:699-708.

Gilcrease, M.Z. (2007). "Integrin Signaling in Epithelial Cells," *Cancer Letters* 247:1-25.

Gong, J. et al. (Jan. 1997). "Role of $\alpha_5 \beta_1$ Integrin in Determining Malignant Properties of colon Carcinoma Cells," *Cell Growth & Differentiation* 8:83-90.

Holt, L.J. et al. (Nov. 2003). "Domain Antibodies: Proteins for Therapy," *Trends in Biotechnology* 21 (11):484-490.

Humpries, J.D. et al. (Mar. 18, 2005). "Dual Functionality of the Anti-β1 Integrin Antibody, 12GIO, Exemplifies Agonistic Signalling From the Ligand Binding Pocket of Integrin Adhesion Receptors," *Journal of biological Chemistry* 280(11):10234-10243.

International Search Report mailed on Sep. 25, 2008, for PCT Application No. PCT/US2007/064572, filed on Mar. 21, 2007, nine pages.

Jin, H. et al. (Feb. 9, 2004). "Integrins: Role in Cancer Development and as Treatment Targets," *Br J Cancer* 90(3):561-565.

Kim, S. et al. (Apr. 2000). "Regulation of Angiogenesis in Vivo by Ligation of Integrin $\alpha_5 \beta_1$ With the Central Cell-Binding Domain of Fibronetin," *American Journal of Pathology* 156(4):1345-1362.

Kirsh, M. et al. (Oct.-Nov. 2001). "Anti-Angiogenic Treatment Strategies for Malignant Brain Tumors," *J. Neurooncol.* 50(1-2):149-163.

Koivunen, E. et al. (Feb. 1994). "Isolation of a Highly Specific Ligand for the $\alpha_5 \beta_1$ Integrin From a Phage Display Library," *The Journal of Cell Biology* 124(3):373-380.

Liapis, H. et al. (Apr. 1997). "Expression of $\alpha_v \beta_3$ Integrin is Less Frequent in Ovarian Epithelial Tumors of Low Malignant Potential in Contrast to Ovarian Carcinomas," *Human Pathology* 28(4):443-449.

Lyseng-Williamson, K.A. et al. (2006). "Bevacizumab: A Review of its Use in Advanced Colorectal Cancer, Breast Cancer, and NSCLC," *American Journal of Cancer* 5(1):43-60.

Magnussen, A. et al. (Apr. 1, 2005). "Rapid Access of Antibodies to $\alpha_5 \beta_3$ Integrin Overexpressed on the Luminal Surface of Tumor Blood Vessels," *Cancer Research* 65(7):2712-2721.

Mettouchi, A. et al. (2006). "Distinct Roles of β1 Integrins During Angiogenesis," *European Journal of Cell Biology* 85:243-247.

Mould, A.P. et al. (Jul. 11, 1997). "Defining the Topology of Integrin α5β1-Fibronectin Interactions Using Inhibitory Anti-α5 and Anti-β1 Monoclonal Antibodies," *The Journal of Biological Chemistry* 272(28):17283-17292.

Mousa, S.A. (1999). "Anti-Integrins as a Potential Therapeutic Target in Angiogenesis," *Expert Opinion on Therapeutic Patents* 9(9):1237-1248.

Muether, P. et al. (May 1, 2005). "Integrin α5β1-Inhibiting Small Molecule Reduces Corneal Neovascularisation," Database Biosis [online], Biosciences Information Services (Database Accession No. PREV200600052329) 46:460, two pages.

Newton, S.A. et al. (Feb. 23, 1995). "Inhibition of Experimental Metastasis of Human Breast Carcinoma Cells in Athymic Nude Mice by Anti-$\alpha_5 \beta_1$ Fibronectin Receptor Integrin Antibodies," *International Journal of Oncology* 6:1063-1070.

Orecchia, A. et al. (Sep. 1, 2003). "Vascular Endothelial Growth Factor Receptor-1 is Deposited in the Extracellular Matrix by Endothelial Cells and is a Ligand for the α5 β1 Integrin," *Journal of Cell Science* 116(17):3479-3489.

Pan, Q. et al. (Jan. 2007). "Blocking Neuropilin-1 Function Has an Additive Effect with Anti-VEGF to Inhibit Tumor Growth," *Cancer Cell* 11:53-67.

Parsons-Wingerter, P. (Jul. 2005). "Uniform Overexpression and Rapid Accessibility of $\alpha_5 \beta_1$ Integrin on Blood Vessels in Tumors," *American Journal of Pathology* 167(1):193-211.

Schiller, J.H. et al. (Dec. 15, 1995). "Loss of the Tumorgenic Phenotype With in Vitro, but not in Vivo, Passaging of a Novel Series of Human Bronchial Epithelial Cell Lines: Possible Role of an $\alpha_{5/} \beta_{1-}$ Integrin-Fibronectin Interaction," *Cancer Research* 55:6215-6221.

Schreiner, C.L. et al. (Mar. 26, 1993). "Defective Vasculature in Fibronectin-Receptor-Deficient CHO Cell Tumors in Nude Mice," *International Journal of Cancer* 55:436-441.

Serini, G. et al. (2006, e-pub. Dec. 2, 2005). "Integrins and Angiogenesis: A Sticky Business," *Experimental Cell Research* 312:651-658.

Shibata, K. et al. (Dec. 1, 1997). "Fibronectin Secretion From Human Peritoneal Tissue Induces $M_r$ 92,000 Type IV Collagenase Experssion and Invasion in Ovarion Cancer Cell Lines," *Cancer Research* 57:5416-5420.

Smit, J.W.A. et al. (1998). "Role of Integrins in the Attachment of Metastatic Follicular Thyroid Carcinoma Cells Lines to Bone," *Thyroid* 8(1):29-36.

Sone, H. et al. (Feb. 23, 2001). "Neutralization of Vascular Endothelial Growth Factor Prevents Collagen-Induced Arthritis and Ameliorates Established Disease in Mice," *Biochemical and Biophysical Research Communication* 281(2):562-568.

Stoeltzing, O. et al. (2003). "Inhibition of Integrin $\alpha_5 \beta_1$ Function With a Small Peptide (ATN-161) Plus Continuous 5-FU Infusin Reduces Colorectal Liver Metastases and Improves Survival in Mice," *Int. J. Cancer* 104:496-503.

Tanaka, R. et al. (Nov. 1, 2005). "Elastic Plasma-Protein-Film Blended with Platelet-Releasate Accelerates Healing of Diabetic Mouse Skin Wounds," Abstract No. 1895, *Blood* 106(11):583A, three pages.

Thorpe, P.E. et al. "Selective Killing of Proliferating Vascular Endothelial Cells by an Anti-Fibronectin Receptor Immunotoxin," abstract only, p. 24.

Van Der Pluijm, G. et al. (Dec. 1997). "Attachment Characteristics and Involvement of Integrins in Adhesion of Breast Cancer Cell Lines to Extracellular Bone Matrix Components," *Laboratory Investigation* 77(6):665-675.

Varner, J.A. (Jun. 1995). "Integrin $\alpha_5 \beta_1$ Expression Negatively Regulates Cell Growth: Reversal by Attachment to Fibronectin," *Molecular Biology of the Cell* 6:725-740.

Written Opinion mailed on Sep. 25, 2008, for PCT Application No. PCT/US2007/064572, filed on Mar. 31, 2007, eighteen-pages.

Yamada, K.M. et al. (Aug. 1, 1990). "Monoclonal Antibody and Synthetic Peptide Inhibitors of Human Tumor Cell Migration," *Cancer Research* 50:4485-4496.

Hermanson, G.T. (1996). "Antibody Modification and Conjugation," Chapter 10 in *Bioconjugate Techniques*, Academic Press, Inc., San Diego, California, p. 456.

Paul, W. (1984). *Fundamental Immunology*, Raven Press Books, Ltd., New York, New York, p. 40. (Russian Only.).

Ramakrishnan, V. et al. (Oct. 6, 2005). "Preclinical Evaluation of an Anti-$\alpha 5 \beta 1$ Integrin Antibody as a Novel Anti-Angiogenic Agent," *Journal of Experimental Therapeutics and Oncology*, Rapid Science Publishers, London, GB, 5(4):273-286. (Accepted Jun. 1, 2006).

Roitt, I. et al. (2000). Immunology, 5th Edition, Mosby London, England, pp. 110. (Russian Only.).

Rudikoff, S. et al. (Mar. 1982). "Single Amino Acid Substitution Altering Antigen-Binding Specificity," *Proc. Natl. Acad. Sci.* USA 79:1979-1983.

Sakahara, H. et al. (Jul. 1985). "Effect of DTPA Conjugation on the Antigen Binding Activity and Biodistribution of Monoclonal Antibodies Against $\alpha$-Fetoprotein," *J. Nucl. Med.* 26(7):750-755.

Wikipedia. (Sep. 13, 2011). "Competitive Inhibition," located at <http://en.wikipedia.org/wiki/Competitiive_inhibition>, last visited Oct. 3, 2011.

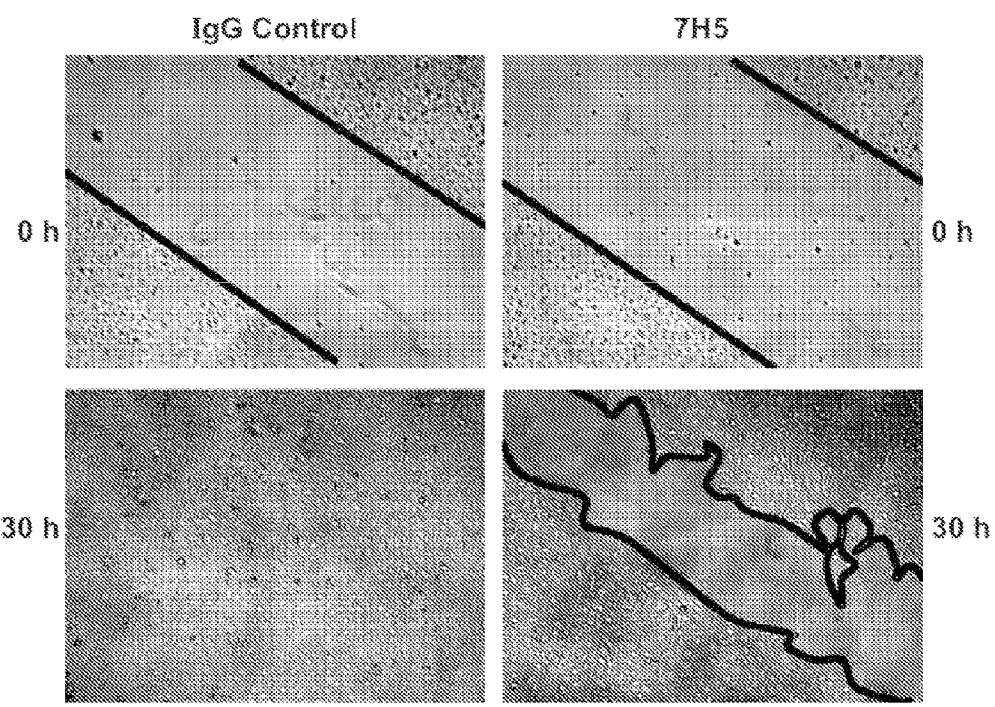
FIG. 6A IgG Control 0 h
FIG. 6C 7H5 0 h
FIG. 6B IgG Control 30 h
FIG. 6D 7H5 30 h

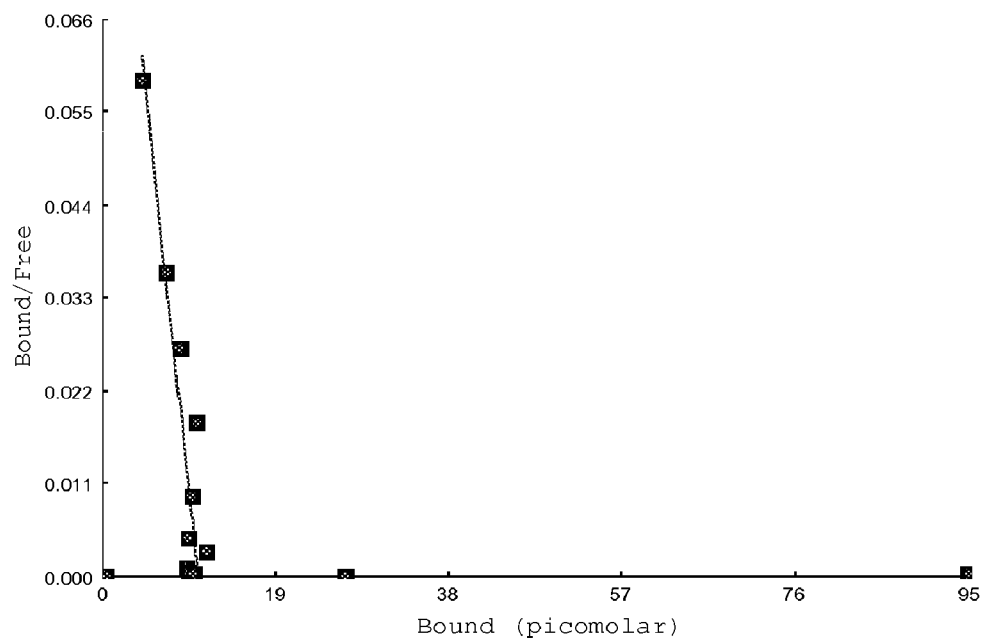
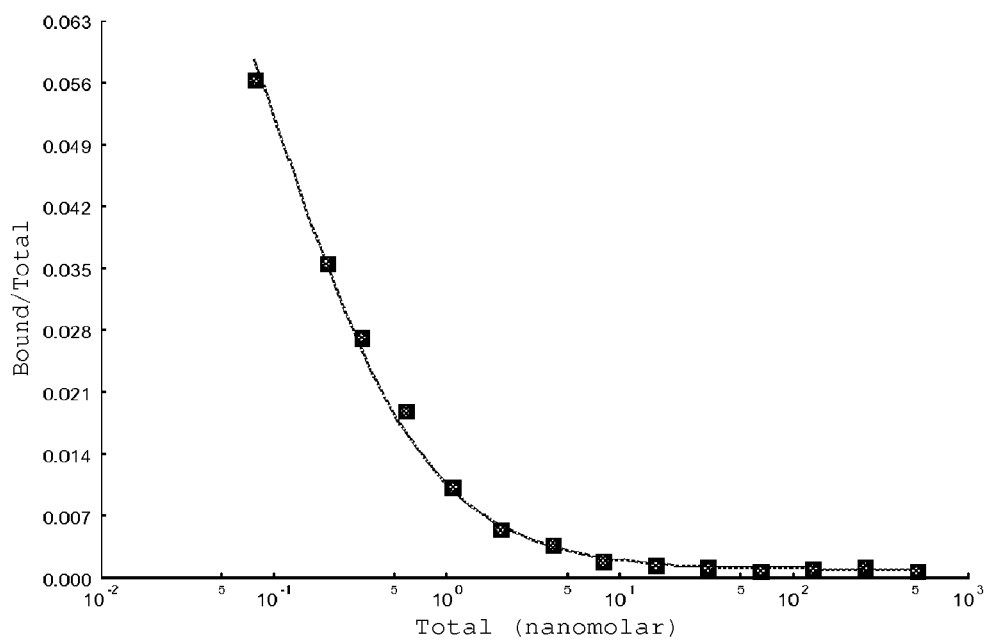
FIG. 14

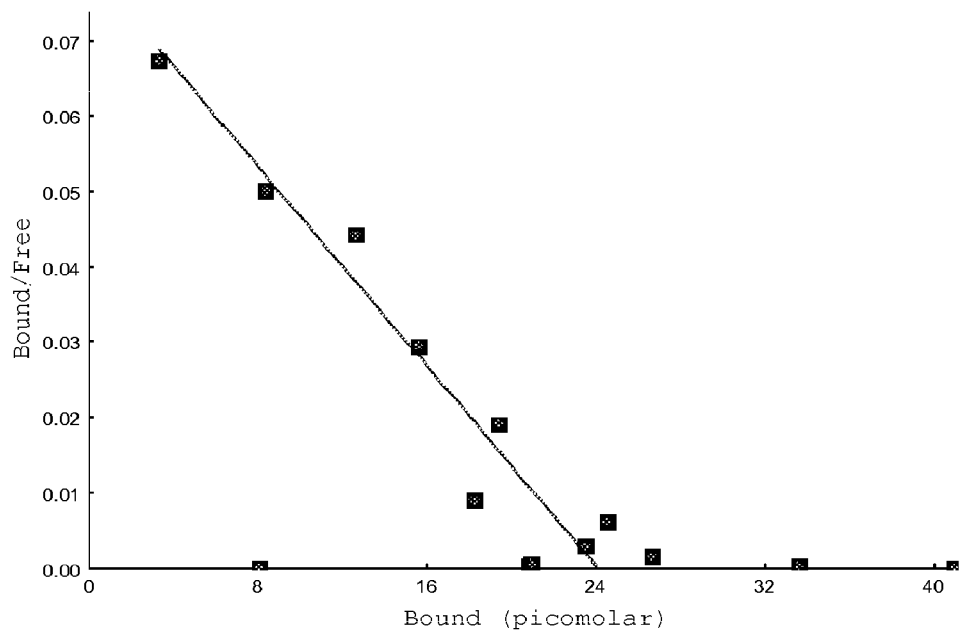
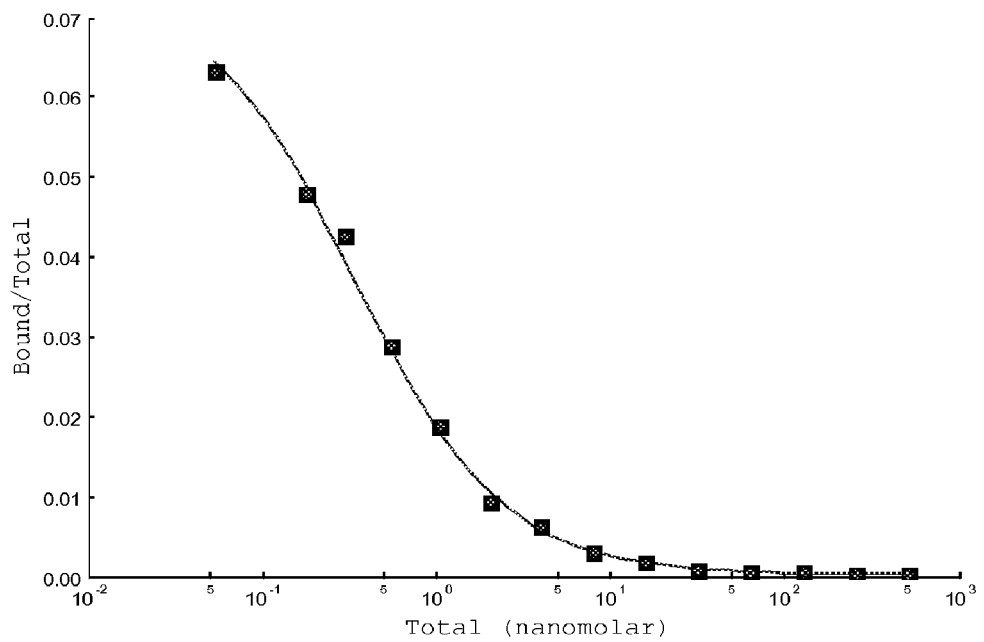
FIG. 15

ANTI-ALPHA5/BETA1 ANTIBODY

CROSS REFERENCE TO RELATED APPLICATIONS

This application is a continuation application of U.S. patent application Ser. No. 12/293,382, which is a national phase application of PCT/US07/64572, filed on Mar. 21, 2007, which claims the priority benefit of U.S. Provisional Patent Application No. 60/784,704, filed Mar. 21, 2006, U.S. Provisional Patent Application No. 60/785,330, filed Mar. 22, 2006, and U.S. Provisional Patent Application No. 60/871,743, filed Dec. 22, 2006, the disclosures of each of which are herein incorporated by reference in their entirety.

FIELD OF THE INVENTION

The present invention relates to the use of VEGF antagonists and alpha5beta1 antagonists for treating cancer and inhibiting angiogenesis and/or inhibited vascular permeability, including in abnormal angiogenesis in diseases. The present invention also relates to use of a VEGFR agonists and alpha5beta1 agonists to promote angiogenesis and vascular permeability. The present invention also relates to anti-alpha5beta1 antibodies, compositions and kits comprising them and methods of making and using them.

BACKGROUND OF THE INVENTION

The important role of VEGF-A in pathological and non-pathological angiogenesis is well established. Administration of VEGF in in vivo models induces a potent angiogenic response (Plouet, J et al., (1989) EMBO J. 8:3801-3808; Leung, D. W., et al., (1989) Science 246:1306-1309). Loss of a single VEGF-A allele gave rise to an embryonic lethality in mice (Carmeliet, P., et al., (1996) Nature 380:435-439; Ferrara, N et al., (1996) Nature 380:439-442). VEGF is also known as a vascular permeability factor due to its ability to induce vascular leakage (Senger, D. R. et al., (1995) Science 219:983-985; Dvorak, H. F., et al., (1995) Am. J. Pathol. 146:1029-1039). Thus, VEGF-A is involved in the developmental, reproductive and bone angiogenesis in addition to other non-pathological angiogenesis.

VEGF-A binds to two receptor tyrosine kinases (RTK), VEGFR-1 (Flt-1) and VEGFR-2 (KDR, Flk-1). VEGFR-2 is generally thought to be the major mediator of the mitogenic, angiogenic and permeability-enhancing effects of VEGF-A. In February 2004, the US Food and Drug Administration (FDA) approved bevacizumab, a humanized anti-VEGF (vascular endothelial growth factor)-A monoclonal antibody, for the treatment of metastatic colorectal cancer in combination with 5-fluorouracil (FU)-based chemotherapy regimens. Subsequently, the FDA approved pegaptinib, an aptamer that blocks the 165 amino-acid isoform of VEGF-A, for the treatment of the wet (neovascular) form of age-related macular degeneration (AMD).

Despite these advances, many patients treated with VEGF antagonists eventually succumb to their disease. Consequently there exists a need to develop new medicaments and treatments for treating diseases that are no longer responsive or are only partially responsive to VEGF antagonist therapies. There also exist a need to develop alternative and/or better therapies for treating cancer and diseases worsened, caused by or effected by abnormal angiogenesis.

SUMMARY OF THE INVENTION

The present invention relates to medicaments and methods of treating patients who would benefit from decreased angiogenesis, who are suffering from abnormal angiogenesis and/or who are suffering from a neoplasia. According to one embodiment, the present invention provides a method for inhibiting angiogenesis and/or vascular permeability in a subject comprising the step of administering to the subject a therapeutically effective amount of a VEGF antagonist and an alpha5beta1 antagonist concurrently or sequentially. According to another embodiment, the present invention provides a method for treating a subject suffering from a disease, wherein the subject had been responsive to treatment for the disease with a VEGF antagonist but is partially or no longer responsive to the VEGF antagonist, comprising the step of administering to the subject a therapeutically effective amount of an alpha5beta antagonist. According to another embodiment, the present invention provides a method for treating a subject suffering from a disease, wherein the disease has been resistant or refractory to an alpha5beta antagonist therapy, alone or in combination with chemotherapy, comprising the step of administering to the subject a therapeutically effective amount of a VEGF antagonist.

The present invention also relates to new anti-alpha5beta1 antibodies, kits and compositions comprising them, and methods of making or using them. According to one embodiment, the new anti-alpha5beta1 antibody is the 7H5 antibody or the 7H12 antibody described herein, or a humanized or chimeric form thereof. According to another specific embodiment, the 7H5 antibody or the 7H12 antibody, or humanized or chimeric form thereof, can be in the form of a Fab, Fab', a F(ab')$_2$, single-chain Fv (scFv), an Fv fragment; a diabody, multi-specific antibody and a linear antibody. According to another embodiment, the new anti-alpha5beta1 antibodies can be conjugated to another entity such as, but not limited to, a therapeutic agent or a fluorescent dye or other marker to detect alpha5beta1 in patients or in patient samples. Such new alpha5beta1 antibodies can be used in a variety of therapeutic and diagnostic methods. For example, such anti-alpha5beta1 antibodies can be used in treating abnormal angiogenesis, neoplasia, ocular diseases and autoimmune diseases. Such antibodies can be used for detecting alpha5beta1 protein in patients or patient samples by contacting such antibodies to alpha5beta1 protein in patients or in patient samples and determining qualitatively or quantitatively the anti-alpha5beta1 antibody bound to the alpha5beta1 protein.

According to yet another embodiment, the present invention provides a method of treating cancer in a subject comprising the step of administering a VEGF antagonist and an alpha5beta1 antagonist concurrently or sequentially is provided. According to one preferred embodiment, the cancer is responsive to VEGF antagonist therapies. In another embodiment, a method of treating age related macular degeneration (AMD), including wet age-related macular degeneration, in a subject suffering from AMD comprising the step of administering a therapeutically effective amount of a VEGF antagonist and an alpha5beta1 antagonist concurrently or sequentially. In yet another embodiment, a method of treating an autoimmune disease in a subject comprising the step of administering a therapeutically effective amount of a VEGF antagonist and an alpha5beta1 antagonist concurrently or sequentially is provided.

In one embodiment, the subject to be treated may be administered the VEGF antagonist initially and subsequently treated with the alpha5beta1 antagonist. In another embodiment, the subject is treated with the VEGF antagonist and the alpha5beta1 antagonist simultaneously. According to another embodiment, the subject is treated with the VEGF antagonist until the subject is unresponsive to VEGF antagonist treatment and then the subject is treated with an alpha5beta1 antagonist. In one particular embodiment, the subject is treated with the VEGF antagonist when the cancer is non-invasive or early stage and treated with the alpha5beta1 antagonist when the cancer is invasive. In another embodiment, subject being treated with the alpha5beta1 antagonist has elevated alpha5beta1 levels in a diseased tissue compared to tissue from a subject not suffering from the disease. In this instance, the method can further include the step of detecting alpha5beta1 in the subject, e.g., in a diseased tissue after treatment with a VEGF antagonist. According to one embodiment, the invasive cancer is a metastasized cancer. According to another embodiment, the early stage cancer is a cancer treated by adjuvant therapy (e.g., chemotherapy or surgical removal).

In one preferred embodiment, the subject is suffering from a disease having abnormal angiogenesis. According to another embodiment, the disease is selected from the group consisting of a cancer, an immune disease or an ocular disease. According to one preferred embodiment, the disease is selected from the group consisting of a solid tumor, a metastatic tumor, a soft tissue tumor, a disease having ocular neovascularisation, an inflammatory disease having abnormal angiogenesis, a disease arising after transplantation into the subject and a disease having abnormal proliferation of fibrovascular tissue. According to another preferred embodiment, the cancer is selected from the group consisting of breast cancer (including metastatic breast cancer), cervical cancer, colorectal cancer (including metastatic colorectal cancer), lung cancer (including non-small cell lung cancer), non-Hodgkins lymphoma (NHL), chronic lymphocytic leukemia, renal cell cancer, prostate cancer including hormone refractory prostate cancer, liver cancer, head and neck cancer, melanoma, ovarian cancer, mesothelioma, soft tissue cancer, gastrointestinal stromal tumor, glioblastoma multiforme and multiple myeloma. According to another preferred embodiment, the disease is selected from the group consisting of retinopathy, age-induced macular degeneration (e.g., wet AMD), diabetic macular edema, rubeosis; psoriasis, an inflammatory renal disease, haemolytic uremic syndrome, diabetic nephropathy (e.g., proliferative diabetic retinopathy), arthritis (e.g., psoriatic arthritis, osteoarthritis, rheumatoid arthritis), inflammatory bowel disease, chronic inflammation, chronic retinal detachment, chronic uveitis, chronic vitritis, corneal graft rejection, corneal neovascularization, corneal graft neovascularization, Crohn's disease, myopia, ocular neovascular disease, Pagets disease, pemphigoid, polyarteritis, post-laser radial keratotomy, retinal neovascularization, Sogrens syndrome, ulcerative colitis, graft rejection, lung inflammation, nephrotic syndrome, edema, ascites associated with malignancies, stroke, angiofibroma and neovascular glaucoma. In one embodiment, the subject is further administered a therapeutic agent selected from the group consisting of an anti-neoplastic agent, a chemotherapeutic agent and a cytotoxic agent.

According to one preferred embodiment of this invention, the subject to be treated with an alpha5beta1 antagonist is suffering from a relapse after VEGF antagonist treatment or has become refractory to VEGF antagonist treatment. According to another embodiment, the subject to be treated with an alpha5beta1 antagonist and a VEGF antagonist is suffering from a metastatic cancer or has previously been treated with adjuvant therapy. In one embodiment, the candidate patient is relapsed, refractory or resistant to a chemotherapeutic agents such as irinotecan. Examples of such diseases, include but are not limited to, metastatic colorectal cancer, relapsed metastatic colorectal cancer, metastatic breast cancer, relapsed metastatic breast cancer, metastatic HER2+ breast cancer, adjuvant breast cancer, adjuvant HER2+ breast cancer, metastatic pancreatic cancer, adjuvant colon cancer, adjuvant non-small cell lung cancer, adjuvant rectal cancer, adjuvant non small cell lung cancer, metastatic non small cell lung cancer, metastatic ovarian cancer, metastatic renal cell cancer and adjuvant renal cell cancer.

According to one embodiment, the subject suffering from a disease described herein is administered a maintenance therapy after treatment for the disease with a VEGF antagonist, wherein the maintenance therapy is an alpha5beta1 antagonist alone or sequentially or concurrently with a VEGF antagonist.

According to one preferred embodiment, the VEGF antagonist can be selected from the group consisting of an antibody, an immunoadhesin, a peptibody, a small molecule and a nucleic acid that hybridizes to a nucleic acid molecule encoding VEGF under stringent conditions (e.g., ribozyme, siRNA and aptamer). According to one preferred embodiment, the VEGF antagonist is an antibody.

According to another embodiment, the antibody is a monoclonal antibody. According to one preferred embodiment, the anti-VEGF antibody is capable of being competitively inhibited from binding to human VEGF by the Avastin® antibody. According to another embodiment, the anti-VEGF antibody is human, humanized or chimeric. According one specific embodiment, the anti-VEGF antibody is the Avastin® antibody. According to another embodiment, the anti-VEGF antibody is selected from the group consisting of a Fab, Fab', a F(ab)'$_2$, single-chain Fv (scFv), an Fv fragment; a diabody and a linear antibody. According to another embodiment, the VEGF antagonist is a bispecific antibody that binds VEGF and alpha5beta1 and is an alpha5beta1 antagonist.

According to one preferred embodiment, the alpha5beta1 antagonist can be selected from the group consisting of an antibody, an immunoadhesin, a peptibody, a small molecule and a nucleic acid that hybridizes to a nucleic acid molecule encoding alpha5beta1 under stringent conditions. According to one preferred embodiment, the alpha5beta1 antagonist is an antibody. According to another embodiment, the antibody is a monoclonal antibody. According to further embodiment, the monoclonal antibody is a chimeric antibody such as the anti-human alpha5beta1 antibody known as M200 or F200. According to one embodiment, the anti-alpha5beta1 antibody comprises the VH sequence of SEQ ID NO: 1 and the VL sequence of SEQ ID NO:2. According to another embodiment, the anti-alpha5beta1 antibody comprises the sequence of SEQ ID NO:3 and the sequence of SEQ ID NO:4. According to another embodiment, the anti-alpha5beta1 antibody comprises the sequence of SEQ ID NO:4 and the sequence of SEQ ID NO:5. According to one preferred embodiment, the anti-alpha5beta1 antibody is capable of being competitively inhibited from binding to human alpha5beta1 by the 7H5 antibody or the 7H12 antibody. According to one preferred embodiment, the anti-alpha5beta1 antibody is human, humanized or chimeric. According one specific embodiment, the anti-alpha5beta1 antibody is the 7H5 antibody, the 7H12 antibody, or a chimeric or humanized antibody thereof. According to another embodiment, the anti-alpha5beta1 antibody is selected from the group consisting of a Fab, Fab', a F(ab)'$_2$, single-chain Fv (scFv), an Fv fragment; a diabody and a linear antibody. According to another embodiment, the alpha5beta1 antagonist is a bispecific antibody that binds VEGF and alpha5beta1 and is a VEGF antagonist. According to yet another embodiment, the anti-alpha5beta1 antagonist has an altered effector function. According one embodiment, an anti-alpha5beta1 antibody is altered to decrease or prevent antibody dependent cellular cytotoxicity (ADCC) or complement dependent cytotoxicity (CDC) activity (e.g., by altering the nucleic acid sequence encoding the Fc portion of the antibody). According to yet another embodiment, the anti-alpha5beta1 antibody has been altered to improve its half-life in humans (e.g., by altering the nucleic acid sequence encoding the Fc portion of the antibody).

According to one embodiment, the VEGF antagonist or the alpha5beta1 antagonist is conjugated to a cytotoxic agent or a chemotherapeutic agent. According to another embodiment, the cytotoxic agent is a radioactive isotope or a toxin.

The present invention provides compositions comprising a VEGF antagonist, an alpha5beta1 antagonist and a pharmaceutically acceptable carrier. The present invention also provides articles of manufacture comprising instructions for detecting alpha5beta1 in a subject who has been treated with a VEGF antagonist.

The present invention also relates to use of VEGFR agonists and alpha5beta1 agonists to promote angiogenesis and vascular permeability and compositions comprising VEGF agonists and alpha5beta1 agonists and a pharmaceutically acceptable carrier. The VEGFR agonists and alpha5beta1 agonists combinatorial therapies can used in treating a variety of diseases that would benefit from increased angiogenesis and vascular permeability, including, for example, wound healing such as in treating chronic wounds, acute wounds and normal wounds.

BRIEF DESCRIPTION OF THE DRAWINGS

FIG. 6 are photographs of HUVEC cell migration after treatment with 7H5 at 0 h and 30 h compared to a negative control (IgG).

FIG. 14 shows a scatchard plot of $^{125}$I-7H5 binding to alpha5beta1 on R9ab, a rabbit fibroblast cell line.

FIG. 15 shows a scatchard plot of $^{125}$I-7H12 binding to alpha5beta1 on R9ab, a rabbit fibroblast cell line.

DETAILED DESCRIPTION OF THE INVENTION

Figure 1:
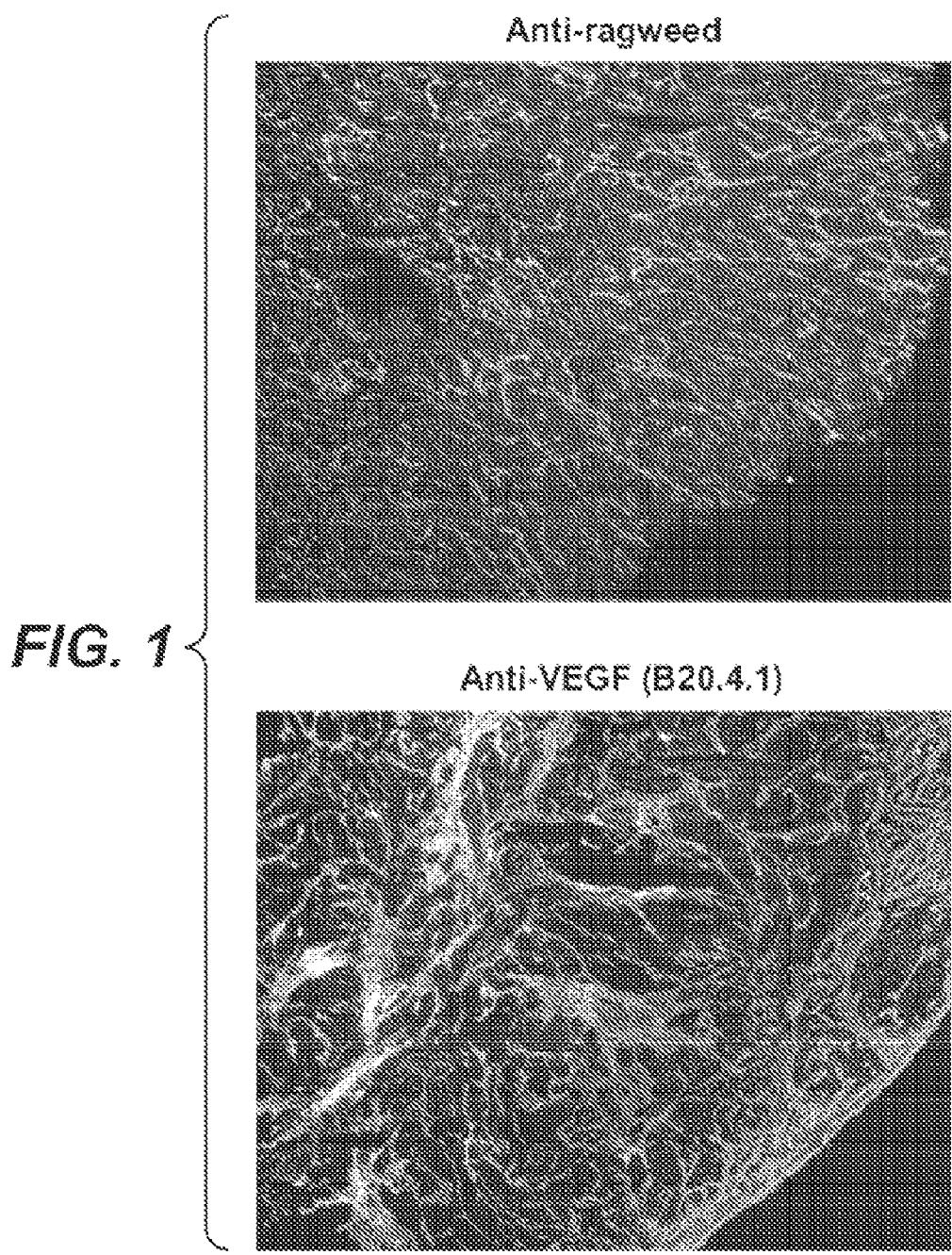
FIG. 1 shows the increase recruitment of alpha5beta1-expressing stromal cells following treatment of HT29 xenograft tumors with the anti-VEGF antibody, B20-4.1.

Without being bound by theory, we propose that increased stromal cell recruitment can bring other vascular growth factors to diseased sites that could compensate for the loss of VEGF activity in patients treated with VEGF antagonist therapies. Targeting a5b1-expressing stromal cells with an anti-a5b1 antibody may result in the reduction of the stromal cells, thereby reducing the production of potential compensatory vascular growth factors. Alternatively, or additionally, we propose that inhibiting endothelial-extracellular matrix interactions, and particularly inhibiting alpha5beta1 binding interactions, will potentiate VEGF antagonist therapies by inhibiting the return of angiogenesis along extracellular matrix tracks left by regressing vessels due to VEGF antagonist therapy. Therefore, treatment with alpha5beta1 antagonists concurrently or after any VEGF antagonist treatment may inhibit vessel recovery from that VEGF antagonist treatment and, consequently, return of neovascular growth.

"Alpha5beta1" or "α5β1" or "a5b1" is an integrin comprising two different proteins (i.e., subunits Alpha5 and beta1). Alpha5beta1 has been shown to bind to fibronectin, L1-CAM and fibrinogen. Alpha5Beta1 integrin has also been called Very Late Activation-5, VLA-5, alpha5beta1, CD49c/CD29, fibronectin receptor, FNR and GPIc-IIa. According to a preferred embodiment, the alpha5beta1 is a human alpha5beta1.

"Alpha5" also known as CD49c, alpha5, integrin alpha5 subunit, VLA-5 alpha subunit, IC subunit of GPIc-IIa and FNR alpha chain has four isoforms generated by alternative splicing (A-D). They vary within their cytoplasmic domains. Amino acid sequences for human isoforms of alpha5 can be found at, e.g., Genbank accession numbers: X07979, U33879, U33882 and U33880, respectively.

"Beta1" also called CD29, beta1, Platelet GPIIa; VLA-beta chain; beta-1 integrin chain, CD29; FNRB; MDF2; VLAB; GPIIA; MSK12 and VLA5B. Amino acid sequences for human Beta1 can be found, e.g., at Genbank Accession No. X06256.

The term "VEGF" or "VEGF" as used herein refers to the 165-amino acid human vascular endothelial cell growth factor and related 121-, 189-, and 206-amino acid human vascular endothelial cell growth factors, as described by Leung et al. Science, 246:1306 (1989), and Houck et al. Mol. Endocrin., 5:1806 (1991), together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF. According to a preferred embodiment, the VEGF is a human VEGF.

A "VEGF antagonist" refers to a molecule capable of neutralizing, blocking, inhibiting, abrogating, reducing or interfering with VEGF activities including its binding to VEGF or one or more VEGF receptors or the nucleic acid encoding them. Preferrably, the VEGF antagonist binds VEGF or a VEGF receptor. VEGF antagonists include anti-VEGF antibodies and antigen-binding fragments thereof, polypeptides that bind VEGF and VEGF receptors and block ligand-receptor interaction (e.g., immunoadhesins, peptibodies), anti-VEGF receptor antibodies and VEGF receptor antagonists such as small molecule inhibitors of the VEGFR tyrosine kinases, aptamers that bind VEGF and nucleic acids that hybridize under stringent conditions to nucleic acid sequences that encode VEGF or VEGF receptor (e.g., RNAi). According to one preferred embodiment, the VEGF antagonist binds to VEGF and inhibits VEGF-induced endothelial cell proliferation in vitro. According to one preferred embodiment, the VEGF antagonist binds to VEGF or a VEGF receptor with greater affinity than a non-VEGF or non-VEGF receptor. According to one preferred embodiment, the VEG antagonist binds to VEGF or a VEGF receptor with a Kd of between 1 uM and 1 pM. According to another preferred embodiment, the VEGF antagonist binds to VEGF or a VEGF receptor between 500 nM and 1 pM.

According a preferred embodiment, the VEGF antagonist is selected from the group consisting of a polypeptide such as an antibody, a peptibody, an immunoadhesin, a small molecule or an aptamer. In a preferred embodiment, the antibody is an anti-VEGF antibody such as the AVASTIN® antibody or an anti-VEGF receptor antibody such as an anti-VEGFR2 or an anti-VEGFR3 antibody. Other examples of VEGF antagonists include: VEGF-Trap, Mucagen, PTK787, SU11248, AG-013736, Bay 439006 (sorafenib), ZD-6474, CP632, CP-547632, AZD-2171, CDP-171, SU-148L3, CHIR-258, AEE-788, SB786034, BAY579352, CDP-79, EG-3306, GW-786034, RWJ-417975/CT6758 and KRN-633.

An "anti-VEGF antibody" is an antibody that binds to VEGF with sufficient affinity and specificity. Preferably, the anti-VEGF antibody of the invention can be used as a therapeutic agent in targeting and interfering with diseases or conditions wherein the VEGF activity is involved. An anti-VEGF antibody will usually not bind to other VEGF homologues such as VEGF-B or VEGF-C, nor other growth factors such as PlGF, PDGF or bFGF. A preferred anti-VEGF antibody is a monoclonal antibody that binds to the same epitope as the monoclonal anti-VEGF antibody A4.6.1 produced by hybridoma ATCC HB 10709. More preferably the anti-VEGF antibody is a recombinant humanized anti-VEGF monoclonal antibody generated according to Presta et al. (1997) Cancer Res. 57:4593-4599, including but not limited to the antibody known as bevacizumab (BV; Avastin®). According to another embodiment, anti-VEGF antibodies that can be used include, but are not limited to the antibodies disclosed in WO 2005/012359. According to one embodiment, the anti-VEGF antibody comprises the variable heavy and variable light region of any one of the antibodies disclosed in FIGS. 24, 25, 26, 27 and 29 of WO 2005/012359 (e.g., G6, G6-23, G6-31, G6-23.1, G6-23.2, B20, B20-4 and B20.4.1). In another preferred embodiment, the anti-VEGF antibody known as ranibizumab is the VEGF antagonist administered for ocular disease such as diabetic neuropathy and AMD.

The anti-VEGF antibody "Bevacizumab (BV)", also known as "rhuMAb VEGF" or "Avastin®", is a recombinant humanized anti-VEGF monoclonal antibody generated according to Presta et al. (1997) Cancer Res. 57:4593-4599. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 daltons and is glycosylated. Other anti-VEGF antibodies include the antibodies described in U.S. Pat. No. 6,884,879 and WO 2005/044853.

The anti-VEGF antibody Ranibizumab or the LUCENTIS® antibody or rhuFabV2 is a humanized, affinity-matured anti-human VEGF Fab fragment. Ranibizumab is produced by standard recombinant technology methods in Escherichia coli expression vector and bacterial fermentation. Ranibizumab is not glycosylated and has a molecular mass of ~48,000 daltons. See WO98/45331 and US20030190317.

"Alpha5Beta1 antagonist" refers to any molecule that inhibits the biological activity of alpha5beta1. According to one preferred embodiment, the antagonist molecule specifically binds alpha5beta1. According to one preferred embodiment, the antagonist molecule binds to alpha5. According to one preferred embodiment, an alpha5beta1 antagonist preferentially binds alpha5beta1 with greater affinity relative to a non-alpha5beta1 integrin. According one preferred embodiment, the antagonist is selected from the group consisting of a polypeptide such as an antibody, a peptibody or an immunoadhesin, a small molecule or aptamer that inhibits the binding of alpha5beta1 to its ligand (particularly, fibronectin) or a nucleic acid that hybridizes under stringent conditions to a nucleic acid molecule encoding alpha5beta1 (e.g., RNAi that interferes with alpha5 expression). A biological activity of alpha5beta1 can be any one, combination or all of the effects selected from the group consisting of (1) binding to fibronectin, (2) enhancing cell migration on fibronectin, (3) increasing survival of cells comprising alpha5beta1 in the presence of fibronectin, (4) increasing proliferation of cells comprising alpha5beta1 in the presence of fibronectin, and (5) increasing tube formation of cells comprising alpha5beta1 in the presence of fibronectin.

Examples of anti-alpha5beta1 antagonist antibodies include M200 and F200 (WO 2004/089988A2), the 7H5 antibody and the 7H12 antibody described herein, and chimeric, fully human and humanized antibodies thereof. For example, M200 and F200 antibodies can be derived from the variable heavy and variable light chains of the mouse anti-human alpha5beta1 antibody, IIA1 (Pharmingen, San Diego, Calif.). Examples of alpha5beta1 small molecule inhibitors include Ac-PHSCN-NH2 (WO-9822617A1) and (S)-2-[(2,4,6-trimethylphenyl)sulfonyl]amino-3-[7-benzyloxycarbonyl-8-(2-pyridinylaminomethyl)-1-oxa-2,7-diazaspiro-(4,4)-non-2-en-3-yl]carbonylamino]propionic acid. According to one preferred embodiment, the anti5beta1 antagonist binds alpha5beta1 and not alphaVbeta3 or alphaVbeta5 or alphaVbeta1. According to one preferred embodiment, the alpha5beta1 antagonist binds to alpha5beta1 with a Kd of between 1 uM and 1 pM. According to another preferred embodiment, the alpha5beta1 antagonist binds to alpha5 with a Kd between 500 nM and 1 pM. According to one preferred embodiment, the alpha5beta1 antibody is an antibody that can compete with the 7H5 antibody or the 7H12 antibody for binding to alpha5beta1 in a competitive binding assay. According to another preferred embodiment, the antibody is an antibody that can be competitively inhibited from binding to alpha5beta1 by the antibody produced from the hybridoma deposited as Alpha5/beta1 7H5.4.2.8 (ATCC No. PTA-7421) or the hybridoma deposited as Alpha5/beta1 7H12.5.1.4 (ATCC No. PTA-7420) on Mar. 7, 2006.

"VEGFR agonist" refers to a molecule that can activate a VEGF receptor or increase its expression. VEGFR agonists include, but are not limited to, e.g., ligand agonists of a VEGFR, VEGF variants, antibodies and active fragments.

"Alpha5Beta1 agonist" refers to a molecule that can activate alpha5Beta1 or increase its expression. Alpha5Beta1 agonists include, but are not limited to, e.g., ligand agonists of alpha5beta1.

Molecules, such as antibodies, characterized by binding to overlapping or the similar areas on a target can be identified by competitive inhibition/binding assays.

In one embodiment, HUVEC or other cells expressing alpha5beta1 are used in a competitive inhibition assay and FACS is used to evaluate binding localities of two anti-alpha5beta1 antibodies relative to each other. For example, HUVEC cells can be washed in conical tube and spun 5 min.@1000 rpm. The pellet is typically washed two times. Then, the cells can be resuspended, counted and kept on ice until use. 100 ul of a first anti-alpha5beta1 antibody (e.g., start at a 1 ug/ml concentration or lower concentration) can be added to the well. Next, 100 µl (e.g., $20 \times 10^5$ cells) of cells can be added into per well and incubated on ice for 30 min. Next, 100 µl of a biotinylated anti-alpha5beta1 antibody (5 µg/ml stock) can be added to each well and incubated on ice for 30 min. The cells are then washed and pelleted for 5 min.@1000 rpm. The supernatant is aspirated. A 2nd antibody R-Phycoerythrin conjugated streptavidin (Jackson 016-110-084) is added to the well (100 µl@1:1000). Next, the plate can be wrapped in foil and incubated on ice 30 min. Following the incubation, the pellet can be washed and pelleted 5 min.@1000 rpm. The pellet can be resuspended ant transferred to micro titertubes for FACS analysis.

An "angiogenic factor or agent" is a growth factor which stimulates the development of blood vessels, e.g., promote angiogenesis, endothelial cell growth, stability of blood vessels, and/or vasculogenesis, etc. For example, angiogenic factors, include, but are not limited to, e.g., VEGF and members of the VEGF family, PlGF, PDGF family, fibroblast growth factor family (FGFs), TIE ligands (Angiopoietins), ephrins, Del-1, fibroblast growth factors: acidic (aFGF) and basic (bFGF), Follistatin, Granulocyte colony-stimulating factor (G-CSF), Hepatocyte growth factor (HGF)/scatter factor (SF), Interleukin-8 (IL-8), Leptin, Midkine, Placental growth factor, Platelet-derived endothelial cell growth factor (PD-ECGF), Platelet-derived growth factor, especially PDGF-BB or PDGFR-beta, Pleiotrophin (PTN), Progranulin, Proliferin, Transforming growth factor-alpha (TGF-alpha), Transforming growth factor-beta (TGF-beta), Tumor necrosis factor-alpha (TNF-alpha), Vascular endothelial growth factor (VEGF)/vascular permeability factor (VPF), etc. It would also include factors that accelerate wound healing, such as growth hormone, insulin-like growth factor-I (IGF-1), VIGF, epidermal growth factor (EGF), CTGF and members of its family, and TGF-alpha and TGF-beta. See, e.g., Klagsbrun and D'Amore, Annu. Rev. Physiol., 53:217-39 (1991); Streit and Detmar, Oncogene, 22:3172-3179 (2003); Ferrara & Alitalo, Nature Medicine 5(12):1359-1364 (1999); Tonini et al., Oncogene, 22:6549-6556 (2003) (e.g., Table 1 listing known angiogenic factors); and, Sato Int. J. Clin. Oncol., 8:200-206 (2003).

The "Kd" or "Kd value" for an anti-VEGF antibody according to this invention is in one preferred embodiment measured by a radiolabeled VEGF binding assay (RIA) performed with the Fab version of the antibody and a VEGF molecule as described by the following assay that measures solution binding affinity of Fabs for VEGF by equilibrating Fab with a minimal concentration of ($^{125}$I)-labeled VEGF (109) in the presence of a titration series of unlabeled VEGF, then capturing bound VEGF with an anti-Fab antibody-coated plate (Chen, et al., (1999) J. Mol Biol 293:865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]VEGF(109) are mixed with serial dilutions of a Fab of interest, e.g., Fab-12 (Presta et al., (1997) Cancer Res. 57:4593-4599). The Fab of interest is then incubated overnight; however, the incubation may continue for 65 hours to insure that equilibrium is reached. Thereafter, the mixtures are transferred to the capture plate for incubation at room temperature for one hour. The solution is then removed and the plate washed eight times with 0.1% Tween-20 in PBS. When the plates had dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized hVEGF (8-109) CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Human VEGF is diluted with 10 mM sodium acetate, pH 4.8, into 5 ug/ml (~0.2 uM) before injection at a flow rate of 5 ul/minute to achieve approximately 10 response units (RU) of coupled protein. Following the injection of human VEGF, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) J. Mol Biol 293:865-881. If the on-rate exceeds $10^6$ $M^{-1}$ $S^{-1}$ by the surface plasmon resonance assay above, then the on-rate is can be determined by using a fluorescent quenching technique that measures the increase or decrease in fluorescence emission intensity (excitation=295 nm; emission=340 nm, 16 nm band-pass) at 25° C. of a 20 nM anti-VEGF antibody (Fab form) in PBS, pH 7.2, in the presence of increasing concentrations of human VEGF short form (8-109) or mouse VEGF as measured in a spectrometer, such as a stop-flow equipped spectrophotometer (Aviv Instruments) or a 8000-series SLM- Aminco spectrophotometer (ThermoSpectronic) with a stirred cuvette. Similar binding assays can be performed for determining the Kd of an anti-alpha5beta1 Fab or antibody using alpha5beta1 as the target.

As used herein, a subject to be treated is a mammal (e.g., human, non-human primate, rat, mouse, cow, horse, pig, sheep, goat, dog, cat, etc.). The subject may be a clinical patient, a clinical trial volunteer, an experimental animal, etc. The subject may be suspected of having or at risk for having a cancer, an immune disease, or any other disease having abnormal angiogenesis, be diagnosed with a cancer, immune disease, or any other disease having abnormal angiogenesis. Many diagnostic methods for cancer, immune disease or any other disease exhibiting abnormal angiogenesis and the clinical delineation of those diseases are known in the art. According to one preferred embodiment, the subject to be treated according to this invention is a human.

The term abnormal angiogenesis occurs when new blood vessels grow either excessively or inappropriately (e.g., the location, timing or onset of the angiogenesis being undesired from a medical standpoint) in a diseased state or such that it causes a diseased state. Excessive, inappropriate or uncontrolled angiogenesis occurs when there is new blood vessel growth that contributes to the worsening of the diseased state or cause of a diseased state, such as in cancer, especially vascularized solid tumors and metastatic tumors (including colon, lung cancer (especially small-cell lung cancer), or prostate cancer), diseases caused by ocular neovascularisation, especially diabetic blindness, retinopathies, primarily diabetic retinopathy or age-induced macular degeneration, choroidal neovascularization (CNV), diabetic macular edema, pathological myopia, von Hippel-Lindau disease, histoplasmosis of the eye, Central Retinal Vein Occlusion (CRVO), corneal neovascularization, retinal neovascularization and rubeosis; psoriasis, psoriatic arthritis, haemangioblastoma such as haemangioma; inflammatory renal diseases, such as glomerulonephritis, especially mesangioproliferative glomerulonephritis, haemolytic uremic syndrome, diabetic nephropathy or hypertensive nephrosclerosis; various inflammatory diseases, such as arthritis, especially rheumatoid arthritis, inflammatory bowel disease, psoriasis, sarcoidosis, arterial arteriosclerosis and diseases occurring after transplants, endometriosis or chronic asthma and more than 70 other conditions. The new blood vessels can feed the diseased tissues, destroy normal tissues, and in the case of cancer, the new vessels can allow tumor cells to escape into the circulation and lodge in other organs (tumor metastases). The present invention contemplates treating those patients that are at risk of developing the above-mentioned illnesses.

Other patients that are candidates for receiving the antibodies or polypeptides of this invention have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, ocular neovascular disease, optic pits, Osler-Weber syndrome (Osler-Weber-Rendu, osteoarthritis, Pagets disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sogrens syndrome, solid tumors, Stargarts disease, Steven's Johnson disease, superior limbic keratitis, syphilis, systemic lupus, Terrien's marginal degeneration, toxoplasmosis, trauma, tumors of Ewing sarcoma, tumors of neuroblastoma, tumors of osteosarcoma, tumors of retinoblastoma, tumors of rhabdomyosarcoma, ulcerative colitis, vein occlusion, Vitamin A deficiency and Wegeners sarcoidosis, undesired angiogenesis associated with diabetes, parasitic diseases, abnormal wound healing, hypertrophy following surgery, injury or trauma, inhibition of hair growth, inhibition of ovulation and corpus luteum formation, inhibition of implantation and inhibition of embryo development in the uterus.

Anti-angiogenesis therapies are useful in the general treatment of graft rejection, lung inflammation, nephrotic syndrome, preeclampsia, pericardial effusion, such as that associated with pericarditis, and pleural effusion, diseases and disorders characterized by undesirable vascular permeability, e.g., edema associated with brain tumors, ascites associated with malignancies, Meigs' syndrome, lung inflammation, nephrotic syndrome, pericardial effusion, pleural effusion, permeability associated with cardiovascular diseases such as the condition following myocardial infarctions and strokes and the like.

Other angiogenesis-dependent diseases according to this invention include angiofibroma (abnormal blood of vessels which are prone to bleeding), neovascular glaucoma (growth of blood vessels in the eye), arteriovenous malformations (abnormal communication between arteries and veins), non-union fractures (fractures that will not heal), atherosclerotic plaques (hardening of the arteries), pyogenic granuloma (common skin lesion composed of blood vessels), scleroderma (a form of connective tissue disease), hemangioma (tumor composed of blood vessels), trachoma (leading cause of blindness in the third world), hemophilic joints, vascular adhesions and hypertrophic scars (abnormal scar formation).

"Treatment" refers to both therapeutic treatment and prophylactic or preventative measures. Those in need of treatment include those already with the disorder as well as those in which the disorder is to be prevented.

The terms "recurrence," "relapse" or "relapsed" refers to the return of a cancer or disease after clinical assessment of the disappearance of disease. A diagnosis of distant metastasis or local recurrence can be considered a relapse.

The term "refractory" or "resistant" refers to a cancer or disease that has not responded to treatment.

The term "adjuvant therapy" refers to treatment given after the primary therapy, usually surgery. Adjuvant therapy for cancer or disease may include immune therapy, chemotherapy, radiation therapy or hormone therapy.

The term "maintenance therapy" refers to scheduled retreatment that is given to help maintain a previous treatment's effects. Maintenance therapy is often given to help keep cancer in remission or prolong a response to a specific therapy regardless of disease progression.

The term "invasive cancer" refers to cancer that has spread beyond the layer of tissue in which it started into the normal surrounding tissues. Invasive cancers may or may not be metastatic.

The term "non-invasive cancer" refers to a very early cancer or a cancer that has not spread beyond the tissue of origin.

The term "progression-free survival" in oncology refers to the length of time during and after treatment that a cancer does not grow. Progression-free survival includes the amount of time patients have experienced a complete response or a partial response, as well as the amount of time patients have experienced stable disease.

The term "progressive disease" in oncology can refer to a tumor growth of more than 20 percent since treatment began—either due to an increase in mass or a spread in the tumor.

A "disorder" is any condition that would benefit from treatment with the antibody. For example, mammals who suffer from or need prophylaxis against abnormal angiogenesis (excessive, inappropriate or uncontrolled angiogenesis) or vascular permeability. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma, head and neck cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), prostate cancer, cancer of the peritoneum, hepatocellular cancer, gastric or stomach cancer including gastrointestinal cancer, pancreatic cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma melanoma, skin carcinomas, Schwannoma oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, and Meigs' syndrome.

"Tumor", as used herein, refers to all neoplastic cell growth and proliferation, whether malignant or benign, and all pre-cancerous and cancerous cells and tissues.

The term "anti-neoplastic composition" or "anti-neoplastic agent" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BAFF, BR3, APRIL, BCMA or VEGF receptor(s), TRAIL/Apo2, and other bioactive and organic chemical agents, etc. Combinations thereof are also contemplated in this invention.

A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly crytophycin 1 and crytophycin 8); dolastatin; duocarmycin (including a the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone mitoxantrone mopidanmol nitraerine, pentostatin; phenamet pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras and EGFR (e.g., erlotinib (Tarceva™)) that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON• toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above.

The term "prodrug" as used in this application refers to a precursor or derivative form of a pharmaceutically active substance (e.g., small molecule) that is less cytotoxic to diseased cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery,* Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

"Isolated," when used to describe the various polypeptides disclosed herein, means polypeptide that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the polypeptide natural environment will not be present. Ordinarily, however, isolated polypeptide will be prepared by at least one purification step.

An "isolated" polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid.

An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50 C; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42 C; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42 C, with a 10 minute wash at 42 C in 0.2×SSC (sodium chloride/sodium citrate) followed by a 10 minute high-stringency wash consisting of 0.1×SSC containing EDTA at 55 C.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Mcgalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code (Table 1) has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

The amino acid sequences described herein are contiguous amino acid sequences unless otherwise specified.

As used herein, the term "immunoadhesin" designates antibody-like molecules that combine the binding specificity of a heterologous protein (an "adhesin") with the effector functions of immunoglobulin constant domains. Structurally, the immunoadhesins comprise a fusion of an amino acid sequence with the desired binding specificity that is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand—such as a VEGFR or a fibronectin ligand. The immunoglobulin constant domain sequence in the immunoadhesin can be obtained from any immunoglobulin, such as IgG-1, IgG-2, IgG-3, or IgG-4 subtypes, IgA (including IgA-1 and IgA-2), IgE, IgD, or IgM. Peptibodies, which often comprise a sequence derived from phage display selection of sequences that specifically bind a target fused to an Fc portion of an immunoglobulin, can be considered immunadhesins herein.

The term "antibody" is used in the broadest sense and specifically covers, for example, single monoclonal antibodies (including agonist, antagonist, and neutralizing antibodies), antibody compositions with polyepitopic specificity, polyclonal antibodies, single chain anti-antibodies, and fragments of antibodies (see below) as long as they specifically bind a native polypeptide and/or exhibit a biological activity or immunological activity of this invention. According to one embodiment, the antibody binds to an oligomeric form of a target protein, e.g., a trimeric form. According to another embodiment, the antibody specifically binds to a protein, which binding can be inhibited by a monoclonal antibody of this invention (e.g., a deposited antibody of this invention, etc.). The phrase "functional fragment or analog" of an antibody is a compound having a qualitative biological activity in common with an antibody to which it is being referred. For example, a functional fragment or analog of an antibody of this invention can be one which can specifically bind to VEGF or alpha5beta1. In one embodiment, the antibody can prevent or substantially reduce the ability of a VEGF to induce cell proliferation.

An "isolated antibody" is one which has been identified and separated and/or recovered from a component of its natural environment. Contaminant components of its natural environment are materials which would interfere with diagnostic or therapeutic uses for the antibody, and can include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for g and c isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FPs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 31-35B (H1), 50-65 (H2) and 95-102 (H3) in the $V_H$ (in one embodiment, H1 is around about 31-35); Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they can be synthesized uncontaminated by other antibodies. The modifier "monoclonal" is not to be construed as requiring production of the antibody by any particular method. For example, the monoclonal antibodies useful in the present invention can be prepared by the hybridoma methodology first described by Kohler et al., *Nature*, 256:495 (1975), or can be made using recombinant DNA methods in bacterial, eukaryotic animal or plant cells (see, e.g., U.S. Pat. No. 4,816, 567). The "monoclonal antibodies" can also be isolated from phage antibody libraries using the techniques described in Clackson et al., *Nature*, 352:624-628 (1991), Marks et al., *J. Mol. Biol.*, 222:581-597 (1991), and the Examples below, for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains can be native sequence constant domains (e.g. human native sequence constant domains) or amino acid sequence variant thereof. Preferably, the intact antibody has one or more effector functions.

"Antibody fragments" comprise a portion of an intact antibody, preferably, the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

The expression "linear antibodies" generally refers to the antibodies described in Zapata et al., Protein Eng., 8(10): 1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "species-dependent antibody" is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

In such embodiments, the extent of binding of the polypeptide, antibody, antagonist or composition to a "non-target" protein will be less than about 10% of the binding of the polypeptide, antibody, antagonist or composition to its particular target protein as determined by fluorescence activated cell sorting (FACS) analysis or radioimmunoprecipitation (RIA). With regard to the binding of a polypeptide, antibody, antagonist or composition to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about 10-7 M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors; and B cell activation. A "native sequence Fc region" comprises an amino acid sequence identical to the amino acid sequence of an Fc region found in nature. Examples of Fc sequences are described in for example, but not limited to, Kabat et al., *Sequences of Immunological Interest*. 5th Ed. Public Health Service, National Institutes of Health, Bethesda, Md. (1991)).

A "variant Fc region" comprises an amino acid sequence which differs from that of a native sequence Fc region by virtue of at least one "amino acid modification" as herein defined. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. In one embodiment, the variant Fc region herein will possess at least about 80% homology, at least about 85% homology, at least about 90% homology, at least about 95% homology or at least about 99% homology with a native sequence Fc region. According to another embodiment, the variant Fc region herein will possess at least about 80% homology, at least about 85% homology, at least about 90% homology, at least about 95% homology or at least about 99% homology with an Fc region of a parent polypeptide.

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNAS-TAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

The term "Fc region-comprising polypeptide" refers to a polypeptide, such as an antibody or immunoadhesin (see definitions below), which comprises an Fc region. The C-terminal lysine (residue 447 according to the EU numbering system) of the Fc region may be removed, for example, during purification of the polypeptide or by recombinantly engineering the nucleic acid encoding the polypeptide. Accordingly, a composition comprising polypeptides, including antibodies, having an Fc region according to this invention can comprise polypeptides populations with all K447 residues removed, polypeptide populations with no (447 residues removed or polypeptide populations having a mixture of polypeptides with and without the K447 residue.

Throughout the present specification and claims, the Kabat numbering system is generally used when referring to a residue in the variable domain (approximately, residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., *Sequences of Proteins of Immunological Interest*, 5th Ed. Public Health Service, National Institutes of Health, Bethesda, Md. (1991) expressly incorporated herein by reference). Unless stated otherwise herein, references to residues numbers in the variable domain of antibodies means residue numbering by the Kabat numbering system. Unless stated otherwise herein, references to residue numbers in the constant domain of antibodies means residue numbering by the EU numbering system.

The terms "Fc receptor" or "FcR" are used to describe a receptor that binds to the Fc region of an antibody. In one embodiment, an FcR of this invention is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol*. 15:203-234 (1997)). The term includes allotypes, such as FcγRIIIA allotypes: FcγRIIIA-Phe158, FcγRIIIA-Val158, FcγRIIA-R131 and/or FcγRIIA-H131. FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med*. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol*. 117:587 (1976) and Kim et al., *J. Immunol*. 24:249 (1994)).

The term "FcRn" refers to the neonatal Fc receptor (FcRn). FcRn is structurally similar to major histocompatibility complex (MHC) and consists of an α-chain noncovalently bound to β2-microglobulin. The multiple functions of the neonatal Fc receptor FcRn are reviewed in Ghetie and Ward (2000) *Annu. Rev. Immunol.* 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

WO00/42072 (Presta) and Shields et al. *J. Biol. Chem.* 9(2): 6591-6604 (2001) describe antibody variants with improved or diminished binding to FcRs. The contents of those publications are specifically incorporated herein by reference.

The "CH1 domain" of a human IgG Fc region (also referred to as "C1" of "H1" domain) usually extends from about amino acid 118 to about amino acid 215 (EU numbering system).

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region. In previous reports, FcR binding was generally attributed to amino acid residues in the lower hinge region of an IgG Fc region.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG)

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

"C1q" is a polypeptide that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The term "binding domain" refers to the region of a polypeptide that binds to another molecule. In the case of an FcR, the binding domain can comprise a portion of a polypeptide chain thereof (e.g. the alpha chain thereof) which is responsible for binding an Fc region. One useful binding domain is the extracellular domain of an FcR alpha chain.

An antibody or peptibody with a variant IgG Fc with "altered" FcR binding affinity or ADCC activity is one which has either enhanced or diminished FcR binding activity (e.g, FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent Kd or IC50 value) than the parent polypeptide or a native sequence IgG Fc. According to some embodiments, the improvement in binding compared to a parent polypeptide is about 3 fold, preferably about 5, 10, 25, 50, 60, 100, 150, 200, up to 500 fold, or about 25% to 1000% improvement in binding. The polypeptide variant which "exhibits decreased binding" to an FcR, binds at least one FcR with lower affinity (e.g, higher apparent Kd or higher IC50 value) than a parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or in the Examples below may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

The polypeptide comprising a variant Fc region which "exhibits increased ADCC" or mediates antibody-dependent cell-mediated cytotoxicity (ADCC) in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using the in vitro ADCC assay as herein disclosed, but other assays or methods for determining ADCC activity, e.g. in an animal model etc, are contemplated. In one embodiment, the preferred variant is from about 5 fold to about 100 fold, e.g. from about 25 to about 50 fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed.

Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

"Human effector cells" are leukocytes which express one or more FcRs and perform effector functions. According to one embodiment, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

Methods of measuring binding to FcRn are known (see, e.g., Ghetie 1997, Hinton 2004) as well as described in the Examples below. Binding to human FcRn in vivo and serum half life of human FcRn high affinity binding polypeptides can be assayed, e.g, in transgenic mice or transfected human cell lines expressing human FcRn, or in primates administered with the Fc variant polypeptides. In one embodiment, specifically the anti-alpha5beta1 antibodies of the invention having a variant IgG Fc exhibits increased binding affinity for human FcRn over a polypeptide having wild-type IgG Fc, by at least 2 fold, at least 5 fold, at least 10 fold, at least 50 fold, at least 60 fold, at least 70 fold, at least 80 fold, at least 100 fold, at least 125 fold, at least 150 fold. In a specific embodiment, the binding affinity for human FcRn is increased about 170 fold.

For binding affinity to FcRn, in one embodiment, the EC50 or apparent Kd (at pH 6.0) of the polypeptide is less than 1 uM, more preferably less than or equal to 100 nM, more preferably less than or equal to 10 nM. In one embodiment, for increased binding affinity to FcγRIII (V158; i.e. low-affinity isotype) the EC50 or apparent Kd less is than or equal to 10 nM, and for FcγRIII (V158; high-affinity isotype) the EC50 or apparent Kd is less than or equal to 3 nM. According to another embodiment, a reduction in binding of an antibody to a Fc receptor relative to a control antibody (e.g., the Herceptin® antibody) may be considered significant relative to the control antibody if the ratio of the values of the absorbances at the midpoints of the test antibody and control antibody binding curves (e.g, $A_{450\ nm(antibody)}/A_{450\ nm(control\ Ab)}$) is less than or equal to 40%. According to another embodiment, an increase in binding of an antibody to a Fc receptor relative to a control antibody (e.g., the Herceptin® antibody) may be considered significant relative to the control antibody if the ratio of the values of the absorbances at the midpoints of the test antibody and control antibody binding curves (e.g., $A_{450\ nm(antibody)}/A_{450\ nm(control\ Ab)}$) is greater than or equal to 125%. See, e.g., Example 16.

A "parent polypeptide" or "parent antibody" is a polypeptide or antibody comprising an amino acid sequence from which the variant polypeptide or antibody arose and against which the variant polypeptide or antibody is being compared. Typically the parent polypeptide or parent antibody lacks one or more of the Fc region modifications disclosed herein and differs in effector function compared to a polypeptide variant as herein disclosed. The parent polypeptide may comprise a native sequence Fc region or an Fc region with pre-existing amino acid sequence modifications (such as additions, deletions and/or substitutions).

Antibodies of this invention can be derived from phage display. As used herein, "library" refers to a plurality of antibody or antibody fragment sequences, or the nucleic acids that encode these sequences, the sequences being different in the combination of variant amino acids that are introduced into these sequences according to the methods of the invention.

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, *Curr. Opin. Struct. Biol.*, 3:355-362 (1992), and references cited therein. In a monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology*, 3:205-0216 (1991).

A "phagemid" is a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

Covalent modifications of polypeptides such as peptibodies, immunoadhesins, antibodies and short peptides are included within the scope of this invention. One type of covalent modification includes reacting targeted amino acid residues of a polypeptide with an organic derivatizing agent that is capable of reacting with selected side chains or the N- or C-terminal residues of the polypeptide. Derivatization with bifunctional agents is useful, for instance, for crosslinking the polypeptide to a water-insoluble support matrix or surface for use in the method for purifying antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Other modifications include the conjugation of toxins to the antagonists such as maytansine and maytansinoids, calicheamicin and other cytotoxic agents.

Another type of covalent modification of the polypeptide comprises linking the polypeptide to one of a variety of non-proteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The polypeptide of the present invention can also be modified if advantageous in a way to form a chimeric molecule comprising the polypeptide fused to another, heterologous polypeptide or amino acid sequence (e.g., immunoadhesins or peptibodies).

In one embodiment, such a chimeric molecule comprises a fusion of the polypeptide with a protein transduction domain which targets the polypeptide for delivery to various tissues and more particularly across the brain blood barrier, using, for example, the protein transduction domain of human immunodeficiency virus TAT protein (Schwarze et al., 1999, Science 285: 1569-72).

In another embodiment, such a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag. Various tag polypeptides and their respective antibodies are known in the art. Examples include poly-histidine (poly-His) or poly-histidine-glycine (poly-His-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule can comprise a fusion of the polypeptide with an immunoglobulin or a particular region of an immunoglobulin. For a bivalent form of the chimeric molecule (e.g., an "immunoadhesin"), such a fusion could be to the Fc region of an IgG molecule. Ig fusions of this invention include polypeptides that comprise approximately or only residues 94-243, residues 33-53 or residues 33-52 of human in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also, U.S. Pat. No. 5,428,130 issued Jun. 27, 1995.

The invention provides methods and compositions for inhibiting or preventing relapse tumor growth or relapse cancer cell growth. In various embodiments, a cancer is relapse tumor growth or relapse cancer cell growth where the number of cancer cells has not been significantly reduced, or has increased, or tumor size has not been significantly reduced, or has increased, or fails any further reduction in size or in number of cancer cells. The determination of whether the cancer cells are relapse tumor growth or relapse cancer cell growth can be made either in vivo or in vitro by any method known in the art for assaying the effectiveness of treatment on cancer cells. A tumor resistant to anti-VEGF treatment is an example of a relapse tumor growth.

An "effective amount" of a polypeptide, antibody, antagonist or composition as disclosed herein is an amount sufficient to carry out a specifically stated purpose. An "effective amount" can be determined empirically and by known methods relating to the stated purpose.

The term "therapeutically effective amount" refers to an amount of an antibody, polypeptide or antagonist of this invention effective to "treat" a disease or disorder in a mammal (aka patient). In the case of cancer, the therapeutically effective amount of the drug can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug can prevent growth and/or kill existing cancer cells, it can be cytostatic and/or cytotoxic. In one embodiment, the therapeutically effective amount is a growth inhibitory amount. In another embodiment, the therapeutically effective amount is an amount that extends the survival of a patient. In another embodiment, the therapeutically effective amount is an amount that improves progression free survival of a patient.

In the case of wound healing, the term "effective amount" or "therapeutically effective amount" refers to an amount of a drug effective to accelerate or improve wound healing in a subject. A therapeutic dose is a dose which exhibits a therapeutic effect on the patient and a sub-therapeutic dose is a dose which does not exhibit a therapeutic effect on the patient treated.

A "chronic wound" refers a wound that does not heal. See, e.g., Lazarus et al., Definitions and guidelines for assessment of wounds and evaluation of healing, Arch. Dermatol. 130: 489-93 (1994). Chronic wounds include, but are not limited to, e.g., arterial ulcers, diabetic ulcers, pressure ulcers, venous ulcers, etc. An acute wound can develop into a chronic wound. Acute wounds include, but are not limited to, wounds caused by, e.g., thermal injury, trauma, surgery, excision of extensive skin cancer, deep fungal and bacterial infections, vasculitis, scleroderma, pemphigus, toxic epidermal necrolysis, etc. See, e.g., Buford, Wound Healing and Pressure Sores, HealingWell.com, published on: Oct. 24, 2001. A "normal wound" refers a wound that undergoes normal wound healing repair.

A "growth inhibitory amount" of a polypeptide, antibody, antagonist or composition of this invention is an amount capable of inhibiting the growth of a cell, especially tumor, e.g., cancer cell, either in vitro or in vivo. A "growth inhibitory amount" of a polypeptide, antibody, antagonist or composition of this invention for purposes of inhibiting neoplastic cell growth can be determined empirically and by known methods or by examples provided herein.

A "cytotoxic amount" of a polypeptide, antibody, antagonist or composition of this invention is an amount capable of causing the destruction of a cell, especially tumor, e.g., cancer cell, either in vitro or in vivo. A "cytotoxic amount" of a polypeptide, antibody, antagonist or composition of this invention for purposes of inhibiting neoplastic cell growth can be determined empirically and by methods known in the art.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS, and relapsing remitting MS, progressive systemic sclerosis, atherosclerosis, arteriosclerosis, sclerosis disseminata, and ataxic sclerosis, inflammatory bowel disease (IBD) (for example, Crohn's disease, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN, membranous proliferative GN (MPGN), including Type I and Type II, and rapidly progressive GN, allergic conditions, allergic reaction, eczema including allergic or atopic eczema, asthma such as asthma bronchiale, bronchial asthma, and auto-immune asthma, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, discoid, alopecia), juvenile onset (Type 1) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis, cerebellar degeneration, neuromyotonia, opsoclonus or opsoclonus myoclonus syndrome (OMS), and sensory neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune inner ear disease (AIED); or autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chororetinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia greata, CREST syndrome (calcinosis, Raynaud's phenomenon, esophageal dysmotility, sclerodactyl), and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myclitis, primary idiopathic myxedema, nephrosis, ophthalmia symphatica, orchitis granulomatosa, pancreatitis, polyradiculitis acuta, pyoderma gangrenosum, Quervain's thyrcoiditis, acquired spenic atrophy, infertility due to antispermatozoan antibodies, non-malignant thymoma, vitiligo, SCID and Epstein-Barr virus-associated diseases, acquired immune deficiency syndrome (AIDS), parasitic diseases such as Leishmania, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

Cancer treatments can be evaluated by, e.g., but not limited to, tumor regression, tumor weight or size shrinkage, time to progression, duration of survival, progression free survival, overall response rate, duration of response, quality of life, protein expression and/or activity. Because the anti-angiogenic agents described herein target the tumor vasculature and not necessarily the neoplastic cells themselves, they represent a unique class of anticancer drugs, and therefore can require unique measures and definitions of clinical responses to drugs. For example, tumor shrinkage of greater than 50% in a 2-dimensional analysis is the standard cut-off for declaring a response. However, the alpha5beta1 antagonists and VEGF antagonists of the invention may cause inhibition of metastatic spread without shrinkage of the primary tumor, or may simply exert a tumouristatic effect. Accordingly, approaches to determining efficacy of the therapy can be employed, including for example, measurement of plasma or urinary markers of angiogenesis and measurement of response through radiological imaging.

Depending on the indication to be treated and factors relevant to the dosing that a physician of skill in the field would be familiar with, the antibodies of the invention will be administered at a dosage that is efficacious for the treatment of that indication while minimizing toxicity and side effects. For the treatment of a cancer, an autoimmune disease or an immunodeficiency disease, the therapeutically effective dosage can be, e.g., in the range of 50 mg/dose to 2.5 g/m2. In one embodiment, the dosage administered is about 250 mg/m2 to about 400 mg/m2 or 500 mg/m2. In another embodiment, the dosage is about 250-375 mg/m2. In yet another embodiment, the dosage range is 275-375 mg/m2.

Treatments for age-related macular degeneration (AMD) can be evaluated by, but it is not limited to, the reducing in the rate of or the prevention of further vision loss. For AMD therapy, efficacy in vivo can, for example, be measured by one or more of the following: assessing the mean change in the best corrected visual acuity (BCVA) from baseline to a desired time, assessing the proportion of subjects who lose fewer than 15 letters in visual acuity at a desired time compared with baseline, assessing the proportion of subjects who gain greater than or equal to 15 letters in visual acuity at a desired time compared with baseline, assessing the proportion of subjects with a visual-acuity Snellen equivalent of 20/2000 or worse at desired time, assessing the NEI Visual Functioning Questionnaire, assessing the size of CNV and amount of leakage of CNV at a desired time, as assessed by fluorescein angiography, etc.

The term "detecting" is intended to include determining the presence or absence of a substance or quantifying the amount of a substance. The term thus refers to the use of the materials, compositions, and methods of the present invention for qualitative and quantitative determinations. In general, the particular technique used for detection is not critical for practice of the invention.

For example, "detecting" according to the invention may include: observing the presence or absence of alpha5 gene product, mRNA molecules, or an alpha5 polypeptide; a change in the levels of an alpha5 polypeptide or amount bound to a target; a change in biological function/activity of an alpha5 polypeptide. In some embodiments, "detecting" may include detecting wild type alpha5 levels (e.g., mRNA or polypeptide levels). Detecting may include quantifying a change (increase or decrease) of any value between 10% and 90%, or of any value between 30% and 60%, or over 100%, when compared to a control. Detecting may include quantifying a change of any value between 2-fold to 10-fold, inclusive, or more e.g., 100-fold.

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

New Anti-Alpha5Beta1 Antibodies

New antibodies that can bind human alpha5beta1 and competitively inhibit the binding of an anti-alpha5beta1 antibody to human alpha5beta1 are provided herein. According to one embodiment, the anti-alpha5beta1 antibody is produced by a hybridoma selected from the group consisting of the hybridoma deposited as Alpha5/beta1 7H5.4.2.8 (ATCC No. PTA-7421) and the hybridoma deposited as Alpha5/beta1 7H12.5.1.4 (ATCC No. PTA-7420) in the ATCC on Mar. 7, 2006. According to another embodiment, the antibody is produced by a hybridoma selected from the group consisting of the hybridoma deposited as Alpha5/beta1 7H5.4.2.8 (ATCC No. PTA-7421) and the hybridoma deposited as Alpha5/beta1 7H12.5.1.4 (ATCC No. PTA-7420) in the ATCC on Mar. 7, 2006. According to yet another embodiment, the antibody comprises the variable heavy (VH) and variable light (VL) domain sequence of the antibody produced by the hybridoma deposited as Alpha5/beta1 7H5.4.2.8 (ATCC No. PTA-7421) in the ATCC on Mar. 7, 2006. In another embodiment, antibody comprises the variable heavy (VH) and variable light (VL) domain sequence of the antibody produced by the hybridoma deposited as Alpha5/beta1 7H12.5.1.4 (ATCC No. PTA-7420) in the ATCC on Mar. 7, 2006. Human or chimeric forms of the antibodies of the deposited hybridomas are also contemplated.

According to one embodiment, the antibody binds a human alpha5beta1 with a Kd between 500 nM and 1 pM. According to another embodiment, the antibody does not bind alphaVbeta3 or alphaVbeta5 or alphaVbeta1. According to another embodiment, the antibody comprises a Fc sequence of a human IgG, e.g., human IgG1 or human IgG4. In another embodiment, a Fc sequence has been altered or otherwise changed so that it that lacks antibody dependent cellular cytotoxicity (ADCC) effector function, often related to their binding to Fc receptors (FcRs). There are many examples of changes or mutations to Fc sequences that can alter effector function. For example, WO00/42072 (Presta) and Shields et al. *J. Biol. Chem.* 9(2): 6591-6604 (2001) describe antibody variants with improved or diminished binding to FcRs. The contents of those publications are specifically incorporated herein by reference. The antibody can be in the form of a Fab, Fab', a F(ab)'$_2$, single-chain Fv (scFv), an Fv fragment; a diabody and a linear antibody. Also, the antibody can be a multi-specific antibody that binds to alpha5beta1 and is an alpha5beta1 antagonist, but also binds one or more other targets and inhibits their function (e.g., VEGF). The antibody can be conjugated to a therapeutic agent (e.g., cytotoxic agent, a radioisotope and a chemotherapeutic agent) or a label for detecting alpha5beta1 in patient samples or in vivo by imaging (e.g., radioisotope, fluorescent dye and enzyme).

Nucleic acid molecules encoding the anti-alpha5beta1 antibodies, expression vectors comprising nucleic acid molecules encoding one or both variable domains, and cells comprising the nucleic acid molecules are also contemplated. These antibodies can be used in the therapies described herein and to detect alpha5beta1 protein in patient samples (e.g., FACS, immunohistochemistry (IHC), ELISA assays) or in patients.

Novel Combinations

New combinations for inhibiting angiogenesis and/or vascular permeability in a subject suffering from a disease, which combinations comprising a VEGF antagonist and an alpha5beta1 antagonist. The VEGF antagonist and the alpha5beta1 antagonist can be administered in concurrent or sequential treatment cycles. Such combinatorial treatments are useful for treating disease, including those diseases having abnormal angiogenesis and/or vascular permeability and would benefit from an anti-angiogenesis therapy. Such diseases include, but are not limited to, cancer, ocular disease, and autoimmune disease. Alternatively, the subject can be treated with the VEGF antagonist and subsequently administered the alpha5beta1 antagonist, e.g., treating with the VEGF antagonist until the subject is unresponsive to VEGF antagonist treatment and then treating the subject is treated with an alpha5beta1 antagonist. According to one embodiment, the subject is treated with the VEGF antagonist when the cancer is non-invasive and then treated with the alpha5beta1 antagonist when the cancer is invasive. Some patients who experience elevated alpha5beta1 levels naturally or in response to VEGF antagonist therapy, compared to non-diseased patients or control, can be especially responsive to this combination treatment. Combinations further comprising a therapeutic agent (e.g., an anti-neoplastic agent, a chemotherapeutic agent, a growth inhibitory agent and a cytotoxic agent) are contemplated. For example, patients who are to be treated with chemotherapy (e.g., irinotecan) and alpha5beta1 antagonists, or who have been treated with chemotherapy and alpha5beta1 antagonists, can benefit from VEGF antagonist therapy. Alternatively, patients who have been treated with chemotherapy and VEGF antagonists can benefit from alpha5beta1 antagonist therapy. In one preferred embodiment, the anti-VEGF antibody is the Avastin® antibody. In another preferred embodiment, the anti-alpha5beta1 antibody is an anti-alpha5beta1 antibody described herein. Kits comprising a VEGF antagonist, an alpha5beta1 antagonist and, optionally, a chemotherapeutic agent are contemplated.

Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary antibody formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the mammal to be treated herein.

The formulation herein may also contain more than one active compound as necessary for the particular indication being treated, preferably those with complementary activities that do not adversely affect each other. For example, it may be desirable to further provide a cytotoxic agent, chemotherapeutic agent, cytokine or immunosuppressive agent (e.g. one which acts on T cells, such as cyclosporin or an antibody that binds T cells, e.g. one which binds LFA-1). The effective amount of such other agents depends on the amount of antibody present in the formulation, the type of disease or disorder or treatment, and other factors discussed above. These are generally used in the same dosages and with administration routes as described herein or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semi-permeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

Articles of Manufacture and Kits

Another embodiment of the invention is an article of manufacture containing materials useful for the treatment of tumors, ocular disease or autoimmune diseases and related conditions. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating the condition and may have a sterile access port (for example the container may be an intravenous solution bag or a vial having a stopper pierceable by a hypodermic injection needle). At least one active agent in the composition is a VEGF antagonist or an alpha5beta1 antagonist or an VEGF agonist or an alpha5beta1 agonist of the invention. The label or package insert indicates that the composition is used for treating the particular condition. The label or package insert will further comprise instructions for administering the antibody composition to the patient. Articles of manufacture and kits comprising combinatorial therapies described herein are also contemplated.

Package insert refers to instructions customarily included in commercial packages of therapeutic products, that contain information about the indications, usage, dosage, administration, contraindications and/or warnings concerning the use of such therapeutic products. In one embodiment, the package insert indicates that the composition is used for treating non-Hodgkins' lymphoma.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for isolation or detection of alpha5beta1 and/or VEGF in patients, optionally in combination with the articles of manufacture. For isolation and purification of alpha5beta1, the kit can contain an anti-alpha5beta1 antibody coupled to beads (e.g., sepharose beads). Kits can be provided which contain the antibodies for detection and quantitation of alpha5beta1 and/or VEGF in vitro, e.g. in an ELISA or a Western blot. As with the article of manufacture, the kit comprises a container and a label or package insert on or associated with the container. For example, the container holds a composition comprising at least one anti-alpha5beta1 antibody of the invention. Additional containers may be included that contain, e.g., diluents and buffers, control antibodies. The label or package insert may provide a description of the composition as well as instructions for the intended in vitro or diagnostic use.

Monoclonal Antibodies

Monoclonal antibodies can be prepared, e.g., using hybridoma methods, such as those described by Kohler and Milstein, *Nature*, 256:495 (1975) or can be made by recombinant DNA methods (U.S. Pat. No. 4,816,567) or can be produced by the methods described herein in the Example section. In a hybridoma method, a mouse, hamster, or other appropriate host animal is typically immunized with an immunizing agent to elicit lymphocytes that produce or are capable of producing antibodies that will specifically bind to the immunizing agent. Alternatively, the lymphocytes can be immunized in vitro.

The immunizing agent will typically include a polypeptide or a fusion protein of the protein of interest or a composition comprising the protein. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice* (New York: Academic Press, 1986), pp. 59-103. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, *J. Immunol.*, 133:3001 (1984); Brodeur et al., *Monoclonal Antibody Production Techniques and Applications* (Marcel Dekker, Inc.: New York, 1987) pp. 51-63.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones can be subcloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies can be monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using, but not limited to, techniques known in the art.

Human and Humanized Antibodies

The antibodies can be humanized antibodies or human antibodies. Humanized forms of non-human (e.g., murine) antibodies are chimeric immunoglobulins, immunoglobulin chains, or fragments thereof (such as Fv, Fab, Fab', F(ab')$_2$, or other antigen-binding subsequences of antibodies) that typically contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody preferably also will comprise at least a portion of an immunoglobulin constant region (Fc), typically that of a human immunoglobulin. Jones et al., *Nature,* 321: 522-525 (1986); Riechmann et al., *Nature,* 332: 323-329 (1988); Presta, *Curr. Op. Struct. Biol.,* 2:593-596 (1992).

Some methods for humanizing non-human antibodies are described in the art and below in the Examples. Generally, a humanized antibody has one or more amino acid residues introduced into it from a source that is non-human. These non-human amino acid residues are often referred to as "import" residues, which are typically taken from an "import" variable domain. According to one embodiment, humanization can be essentially performed following the method of Winter and co-workers (Jones et al., *Nature,* 321: 522-525 (1986); Riechmann et al., *Nature,* 332: 323-327 (1988); Verhoeyen et al., *Science,* 239: 1534-1536 (1988)), by substituting rodent CDRs or CDR sequences for the corresponding sequences of a human antibody. Accordingly, such "humanized" antibodies are antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggemann et al., *Year in Immuno.,* 7:33 (1993); U.S. Pat. Nos. 5,545,806, 5,569,825, 5,591,669 (all of GenPharm); 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; and 5,661, 016, and in the following scientific publications: Marks et al., *Bio/Technology,* 10: 779-783 (1992); Lonberg et al., *Nature,* 368: 856-859 (1994); Morrison, *Nature,* 368: 812-813 (1994); Fishwild et al., *Nature Biotechnology,* 14: 845-851 (1996); Neuberger, *Nature Biotechnology,* 14: 826 (1996); Lonberg and Huszar, *Intern. Rev. Immunol.,* 13: 65-93 (1995).

Alternatively, phage display technology (McCafferty et al., Nature 348:552-553 [1990]) can be used to produce human antibodies and antibody fragments in vitro, from immunoglobulin variable (V) domain gene repertoires from unimmunized donors. According to one embodiment of this technique, antibody V domain sequences are cloned in-frame into either a major or minor coat protein gene of a filamentous bacteriophage, such as M13 or fd, and displayed as functional antibody fragments on the surface of the phage particle. Phage display can be performed in a variety of formats, e.g., as described below in the Examples section or as reviewed in, e.g., Johnson, Kevin S. and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573, 905.

As discussed above, human antibodies may also be generated by in vitro activated B cells (see U.S. Pat. Nos. 5,567,610 and 5,229,275).

Human antibodies can also be produced using various techniques known in the art, including phage display libraries. Hoogenboom and Winter, *J. Mol. Biol.,* 227: 381 (1991); Marks et al., *J. Mol. Biol.,* 222: 581 (1991). The techniques of Cole et al. and Boerner et al. are also available for the preparation of human monoclonal antibodies. Cole et al., *Monoclonal Antibodies and Cancer Therapy,* Alan R. Liss, p. 77 (1985) and Boerner et al., *J. Immunol.,* 147(1): 86-95 (1991).

Multi-Specific Antibodies

Multi-specific antibodies are monoclonal, preferably human or humanized, antibodies that have binding specificities for two or more different antigens (e.g., bispecific antibodies have binding specificities for at least two antigens). For example, one of the binding specificities can be for the alpha5beta1 antibody, the other one can be for any other antigen. According to one preferred embodiment, the other antigen is a cell-surface protein or receptor or receptor subunit. For example, the cell-surface protein can be a natural killer (NK) cell receptor. Thus, according to one embodiment, a bispecific antibody of this invention can bind alpha5beta1 and bind a VEGF.

Examples of methods for making bispecific antibodies have been described. Traditionally, the recombinant production of bispecific antibodies is based on the co-expression of two immunoglobulin heavy-chain/light-chain pairs, where the two heavy chains have different specificities. Milstein and Cuello, *Nature,* 305: 537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.,* 10: 3655-3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh et al., *Methods in Enzymology,* 121: 210 (1986).

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Nail. Acad. Sci. USA*, 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Heteroconjugate Antibodies

Heteroconjugate antibodies are composed of two covalently joined antibodies. Such antibodies have, for example, been proposed to target immune-system cells to unwanted cells (U.S. Pat. No. 4,676,980), and for treatment of HIV infection. WO 91/00360; WO 92/200373; EP 03089. It is contemplated that the antibodies can be prepared in vitro using known methods in synthetic protein chemistry, including those involving crosslinking agents. For example, immunotoxins can be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the invention with respect to effector function, so as to enhance, e.g., the effectiveness of the antibody in treating cancer. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). See, Caron et al., *J. Exp. Med.*, 176: 1191-1195 (1992) and Shopes, J. *Immunol.*, 148: 2918-2922 (1992). Homodimeric antibodies with enhanced anti-tumor activity can also be prepared using heterobifunctional crosslinkers as described in Wolff et al., *Cancer Research,* 53: 2560-2565 (1993). Alternatively, an antibody can be engineered that has dual Fc regions and can thereby have enhanced complement lysis and ADCC capabilities. See, Stevenson et al., *Anti-Cancer Drug Design,* 3: 219-230 (1989).

Mutations or alterations in the Fc region sequences can be made to improve FcR binding (e.g., FcgammaR, FcRn). According to one embodiment, an antibody of this invention has at least one altered effector function selected from the group consisting of ADCC, CDC, and improved FcRn binding compared to a native IgG or a parent antibody. Examples of several useful specific mutations are described in, e.g., Shields, R L et al. (2001) *JBC* 276(6)6591-6604; Presta, L. G., (2002) *Biochemical Society Transactions* 30(4):487-490; and WO publication WO00/42072.

According to one embodiment, the Fc receptor mutation is a substitution at least one position selected from the group consisting of: 238, 239, 246, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 332, 333, 334, 335, 337, 338, 340, 360, 373, 376, 378, 382, 388, 389, 398, 414, 416, 419, 430, 434, 435, 437, 438 or 439 of the Fc region, wherein the numbering of the residues in the Fc region is according to the EU numbering system.

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as his (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, WO94/11026.

In another embodiment, the antibody can be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Immunoliposomes

The antibodies disclosed herein can also be formulated as immunoliposomes. Liposomes containing the antibody are prepared by methods known in the art, such as described in Epstein et al., *Proc. Nail. Acad. Sci. USA,* 82: 3688 (1985); Hwang et al., *Proc. Natl. Acad. Sci. USA,* 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286-288 (1982) via a disulfide-interchange reaction. A chemotherapeutic agent (such as Doxorubicin) is optionally contained within the liposome. See, Gabizon et al., *J. National Cancer Inst.*, 81(19): 1484 (1989).

Pharmaceutical Compositions of Antibodies and Polypeptides

Antibodies specifically binding a polypeptide identified herein, as well as other molecules identified by the screening assays disclosed hereinbefore, can be administered for the treatment of various disorders as noted above and below in the form of pharmaceutical compositions.

Lipofectins or liposomes can be used to deliver the polypeptides and antibodies or compositions of this invention into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993).

The formulation herein can also contain more than one active compound as necessary for the particular indication being treated, preferably those with complementary activities that do not adversely affect each other. Alternatively, or in addition the composition can comprise an agent that enhances its function, such as, for example, a cytotoxic agent, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

Diagnostic Use and Imaging

Labeled antibodies, and derivatives and analogs thereof, which specifically bind to a polypeptide can be used for diagnostic purposes to detect, diagnose, or monitor diseases and/or disorders associated with the expression, aberrant expression and/or activity of a polypeptide of the invention. According to one preferred embodiment, the antibodies of this invention can be used in diagnostic assays or imaging assays that involve injection of the antibody into the subject. The invention provides for the detection of aberrant expression of a VEGF or alpha5beta1 polypeptide, comprising (a) assaying the expression of the polypeptide in cells (e.g., tissue) or body fluid of an individual using one or more antibodies of this invention and (b) comparing the level of gene expression with a standard gene expression level, whereby an increase or decrease in the assayed gene expression level compared to the standard expression level is indicative of aberrant expression.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

Diagnosis of a disease or disorder associated with expression or aberrant expression of VEGF and/or alpha5beta1 in an animal, preferably a mammal and most preferably a human can comprise the step of detecting alpha5beta1 and/or VEGF molecules in the mammal. In one embodiment, after administering a VEGF antagonist, diagnosis comprises: (a) administering (for example, parenterally, subcutaneously, or intraperitoneally) to a mammal an effective amount of a labeled anti-alpha5beta1 antibody (b) waiting for a time interval following the administering for permitting the labeled molecule to preferentially concentrate at sites in the subject where the alpha5beta 1 molecule is expressed (and for unbound labeled molecule to be cleared to background level); (c) determining background level; and (d) detecting the labeled molecule in the subject, such that detection of labeled molecule above the background level indicates that the subject has a particular disease or disorder associated with expression or aberrant expression of alpha5beta1. Background level can be determined by various methods including, comparing the amount of labeled molecule detected to a standard value previously determined for a particular system.

According to one specific embodiment, alpha5beta1 polypeptide expression or overexpression is determined in a diagnostic or prognostic assay after administration of a VEGF antagonist therapeutic agent by evaluating levels of alpha5beta1 present on the surface of a cell (e.g., a via an immunohistochemistry assay using anti-alpha5beta1 antibodies). Alternatively, or additionally, one can measure levels of alpha5beta1 polypeptide-encoding nucleic acid or mRNA in the cell, e.g., via fluorescent in situ hybridization using a nucleic acid based probe corresponding to an alpha5beta1-encoding nucleic acid or the complement thereof; (FISH; see WO98/45479 published October, 1998), Southern blotting, Northern blotting, or polymerase chain reaction (PCR) techniques, such as real time quantitative PCR(RT-PCR). One can also study alpha5beta1 overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., *J. Immunol. Methods* 132:73-80 (1990)). Aside from the above assays, various in vivo assays are available to the skilled practitioner. For example, one can expose cells within the body of the mammal to an antibody which is optionally labeled with a detectable label, e.g., a radioactive isotope, and binding of the antibody to cells in the mammal can be evaluated, e.g., by external scanning for radioactivity or by analyzing a biopsy taken from a mammal previously exposed to the antibody.

All publications (including patents and patent applications) cited herein are hereby incorporated in their entirety by reference, including specifically, U.S. Provisional Application No. 60/784,704, filed Mar. 21, 2006, U.S. Provisional Application No. 60/785,330, filed Mar. 22, 2006; and U.S. Provisional Application No. 60/871,743, filed Dec. 22, 2006.

The following DNA sequences were deposited under the terms of the Budapest Treaty with the American Type Culture Collection (ATCC), 10801 University Blvd., Manassas, Va. 20110-2209, USA as described below:

| Material | Deposit No. | Deposit Date |
| --- | --- | --- |
| Alpha5/beta1 7H5.4.2.8 | PTA-7421 | Mar. 7, 2006 |
| Alpha5/beta1 7H12.5.1.4 | PTA-7420 | Mar. 7, 2006 |

The deposits herein were made under the provisions of the Budapest Treaty on the International Recognition of the Deposit of Microorganisms for the Purpose of Patent Procedure and the Regulations thereunder (Budapest Treaty). This assures maintenance of a viable culture of the deposits for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposits to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. 122 and the Commissioner's rules pursuant to thereto (including 37 C.F.R. 1.14 with particular reference to 886 OG 638).

The assignee of the present application has agreed that if a culture of the materials on deposits should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture*, 1987; Coligan et al., *Current Protocols in Immunology*, 1991.

Throughout this specification and claims, the word "comprise," or variations such as "comprises" or "comprising," will be understood to imply the inclusion of a stated integer or group of integers but not the exclusion of any other integer or group of integers.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1

Recruitment of Alpha5Beta1-Expressing Stromal Cells after Anti-VEGF Therapy

Sections of HT-29 human colorectal carcinoma xenografts that had been treated with anti-VEGF antibody B20-4.1 monotherapy in athymic mice were stained for anti-alpha5beta1 expression. Compared to a control group treated with a control antibody (anti-ragweed antibody) in this study, B20-4.1 monotherapy yielded a median time to endpoint (TTE) that corresponded to little or no activity. The tumors had been measured twice weekly for the duration of 58 days. Animals were euthanized when their tumors reached the endpoint volume of 1000 mm3 or on Day 58, whichever came first, and the (TTE) was calculated for each mouse. Treatment outcome had been determined from percent tumor growth delay (% TGD), defined as the percent increase in median TTE of treated versus control mice, with differences deemed significant at $0.01 \leq P \leq 0.05$, and highly significant at $P < 0.01$ using Logrank analysis. The median TTE value of the control group was 20.6 days. Treatment with B20-4.1 monotherapy yielded a median TTE of 20.1 days that corresponded to no activity.

FIG. 1 shows tumor sections stained with anti-alpha5beta1 antibody. An increased stromal cell recruitment was observed after anti-VEGF treatment. These stromal cells are positive for integrin a5b1 (light green stain).

Example 2

Anti-Alpha5Beta1 Antibodies

Mice were injected with purified human alpha5beta1 (Chemicon CC1027). Plasmacytoma cells expressing anti-alpha5beta1 antibodies were isolated and transformed into hybridoma cell lines. Two hybridoma cell lines designated 7H5.4.2.8 and 7H12.5.1.4 were deposited with the ATCC. See above. The antibody produced from the 7H5.4.2.8 hybridoma is a mIgG2a Kappa antibody (also referred to herein as the "7H5 antibody"). The antibody produced from the 7H12.5.1.4 hybridoma is a mIgG2b Kappa antibody (also referred to herein as the "7H12 antibody").

Example 3

HUVEC Direct Binding Assay

Tissue cultures containing growing human umbilical vein endothelial cells (HUVEC) were washed twice with PBS. The cells were detached from the culture flask with 3-4 ml of a 5 mM EDTA/PBS solution. Fresh culture media was added to the cells and mixed. An aliquot of the cells in the mixture was counted. Cells were centrifuged and washed with wash buffer (50 mM Tris, 150 mM NaCl, pH7.5) one time. The cell concentration was adjusted so that the cells could be seeded at 25 ul per well onto 96-well MSD high binding plates at 25,000 cells/well or 4,000 cells/well on a 384 well plate (Cat #L11XB-1 or #L11XB-2, respectively, Meso Scale Diagnostics, LLC). The cells were incubated 1 hour at room temperature on the plate to allow capture. To block the well, 25 ul of stock buffer (30% fetal bovine serum (FBS) in TBS (50 mM Tris, 150 mM NaCl)+1 mM CaCl2/1 mM MgCl2, pH7.5) was added to the well and incubated at room temperature to for 30 minutes to 1 hour.

Anti-alpha5beta1 antibodies serially diluted with assay buffer (TBS with 1 mMCaCl2/1 mM MgCl2, pH7.2+2-4% FBS) to have a variety of antibody concentrations. The wells were washed twice with wash buffer then blotted dry. 25 uls of antibody dilution were added to a well and then incubated on ice for one your. The wells were washed three times with TBS.

Figure 2:
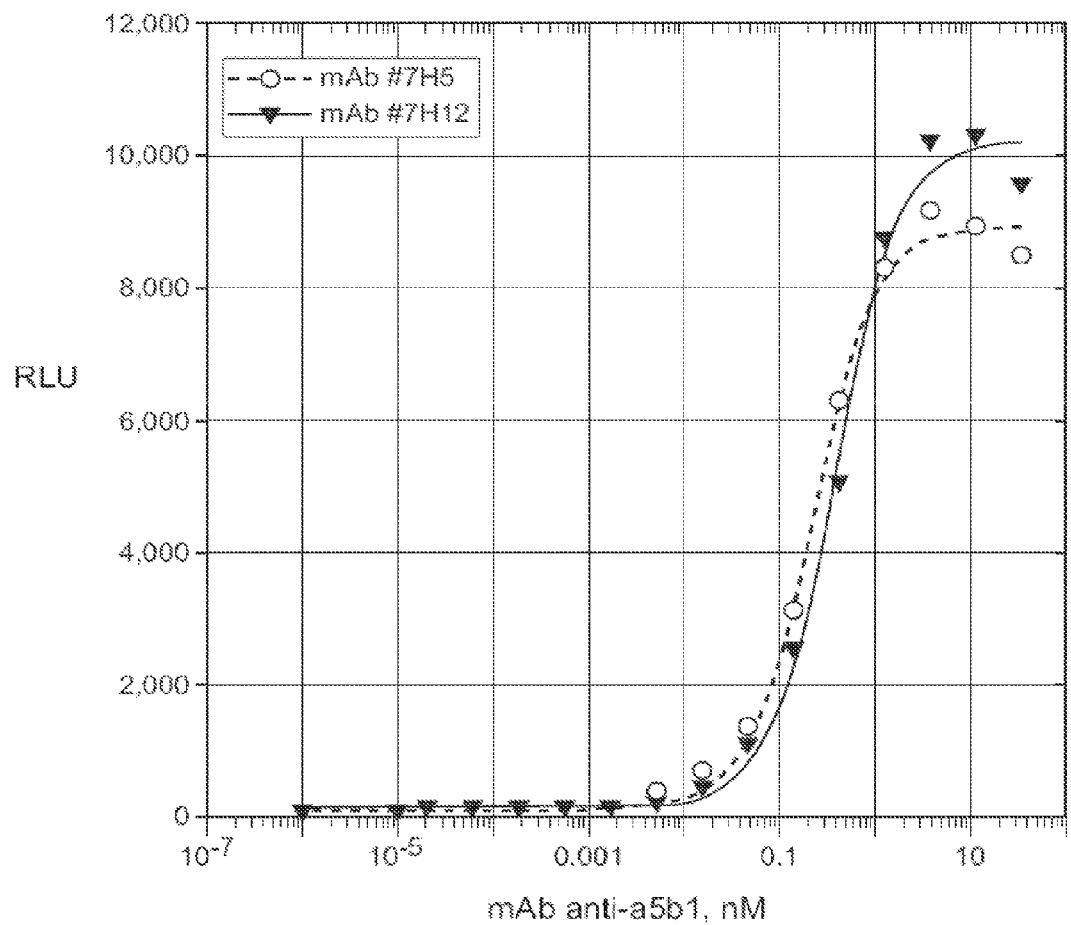
FIG. 2 is a graph showing 7H5 and 7H12 antibodies binding to HUVEC cells in a direct binding assay.

25 uls of a 0.5 ug/ml xmuFc-sulfo-tag solution were added to each well and incubated on ice for 45 minutes to one hour. xmuFc-sulfo-tag is a goat-anti-murine IgG: R23-AC-5, MSD-SA-tag: R32-21-AD-5, on ice for 45 mins to 1 hr. The wells were washed three times with TBS. 150 ul of 2× read buffer was added to each well (4×MSD read buffer, dil to 2× with dH2O, cat #R92TD-1 (surfactant free)). The consequent electrochemiluminescent (ECL) signal was measured by photodiodes and is quantified as a relative light unit using an MSD reader (default 6000 protocol). FIG. 2 shows the results of the HUVEC direct binding assay. The EC50 of the 7H5 antibody was 0.22 nM. The EC50 of the 7H12 antibody was 0.38 nM.

Example 4

Anti-Alpha5Beta1 Antibody FACS Assay

Figure 3:
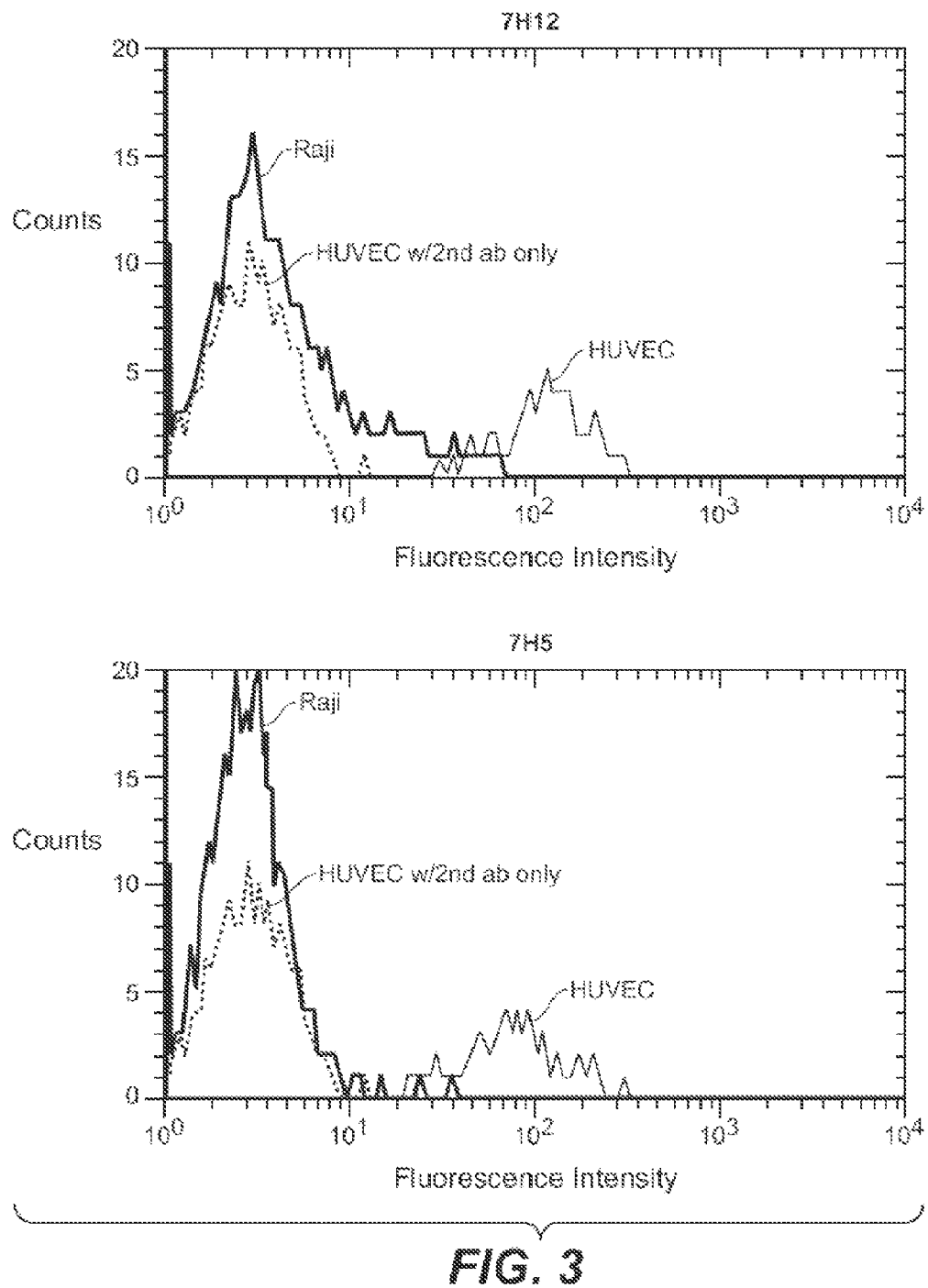
FIG. 3 shows 7H5 and 7H12 antibodies binding to HUVEC but not RAJI cells by FACS analysis.

7H12 or 7H5 antibodies were incubated with either RAJI cells (a cell line that doesn't express alpha5beta1 mRNA) or HUVEC cells (a cell line that expresses high levels of alpha5beta1 mRNA) in 100 ul. The bound cells were detected using a fluorescently conjugated second antibody. FIG. 3 shows via FACS analysis that 7H12 and 7H5 binds to HUVEC cells and not RAJI cells. Using the same techniques with rabbit synoviocyte (HIG-82) or rhesus monkey cells (CL-160 macaca mulatta fibroblasts or CRL-1780 retina endothelial cells), we observed 7H12 and 7H5 binding to rabbit and monkey cells.

Example 5

Cell Adhesion to Fibronectin in the Presence of Anti-Alpha5-Beta1 Antibodies

Fibronectin (Sigma F1141 (bovine) or Roche 1080938 (human)) was diluted to 1 ug/ml in a sodium carbonate buffer. 100 µl of the fibronectin solution was added per well of a NUNC maxisorp 96 well plate and left to bind overnight at 4° C. (NUNC 96 well flat bottom Immuno plates, MaxiSorp N/Ster 439454 (VWR 62409-002)). The wells were then washed with phosphate buffered saline (PBS) and blocked with 1% BSA (Sigma A9418) for at least 30 min. The plates were then washed three times with PBS. 20,000 HUVEC cells were added into each well and incubated with various concentrations of 7H5 or 7H12 in growth media containing 1.4 mM MgCl2 and 1.4 mM CaCl2. The incubation mixture was then added the fibronectin coated plate. Approximately 20,000 cells in the same growth media were added to each control well when no inhibitory antibody was added.

Figure 4:
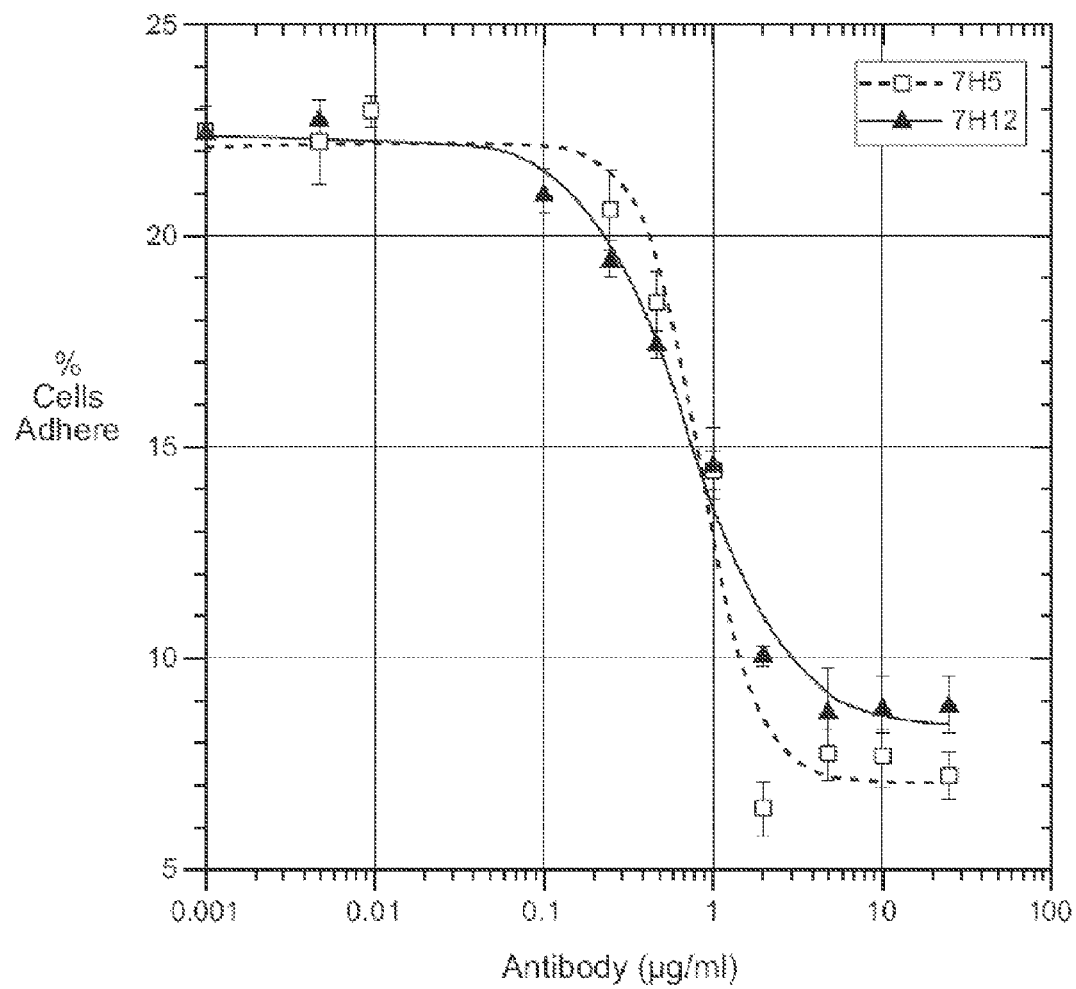
FIG. 4 is a graph showing HUVEC adhesion to fibronectin in the presence of purified 7H5 and 7H12 monoclonal antibodies.

The plates were spun 5 min at 140 g to synchronize contact of cells with substrate. The cells were incubated in a $CO_2$ incubator for various lengths of time (from 0 to 120 min). The length of time of the incubation varied for each cell line. The plates were then washed three times in PBS. All liquid was removed from the wells and frozen at −80° C. The plates were then thawed at room temperature. CyQuant buffer (Molecular Probes CyQuant C7026) was added to the wells and the plate was incubated at room temperature for 10 min. The OD reading was measured. FIG. 4 shows that the IC50 of the 7H5 antibody was 0.85 ug/ml (3.44 nM) and the IC50 of the 7H12 antibody was 0.7 ug/ml (4.38 nM).

Example 6

Proliferation Assay Using HUVEC Cells 96 well plates were coated with fibronectin (1 µg/ml) overnight. The plate was then washed with PBS. 3000-5000 endothelial cells (EC) cells were added per 96 well and allowed to attach to the well completely. Anti-alpha5 antibodies were added (including isotype controls). 3 wells are used for each condition. Cells are then incubated with the antibodies for 1-24 hours. Anti-integrin alpha5beta1 antibodies were tested at several concentrations (e.g., 0 µg/ml, 4 µg/ml, 16 µg/ml, 60 µg/ml, 120 µg/ml).

Figure 5A:
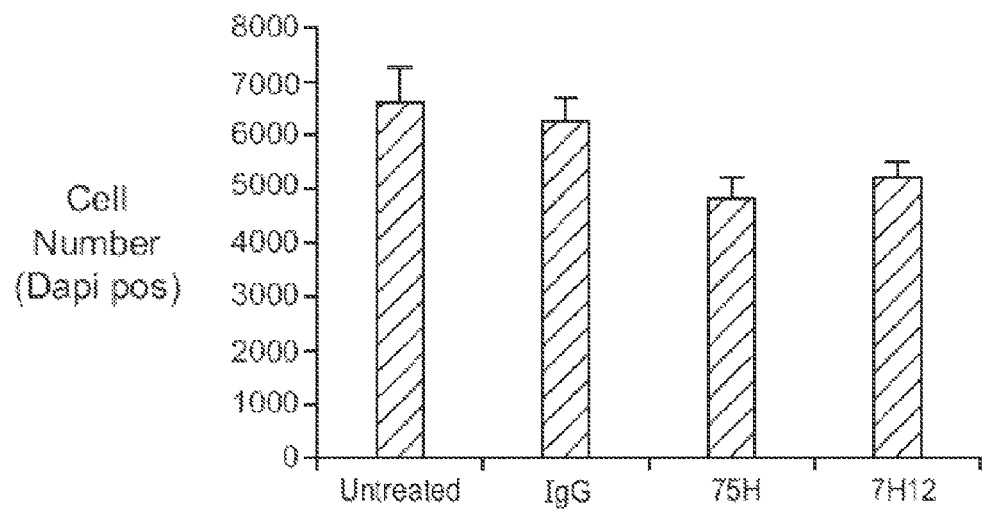
FIG. 5 is (A) a bar graph showing the effect of 7H5 and 7H12 on HUVEC cell proliferation by total cell count and (B) a bar graph showing the effect of 7H5 and 7H12 on HUVEC cell proliferation by Alamar blue staining in another assay.
Figure 5B:
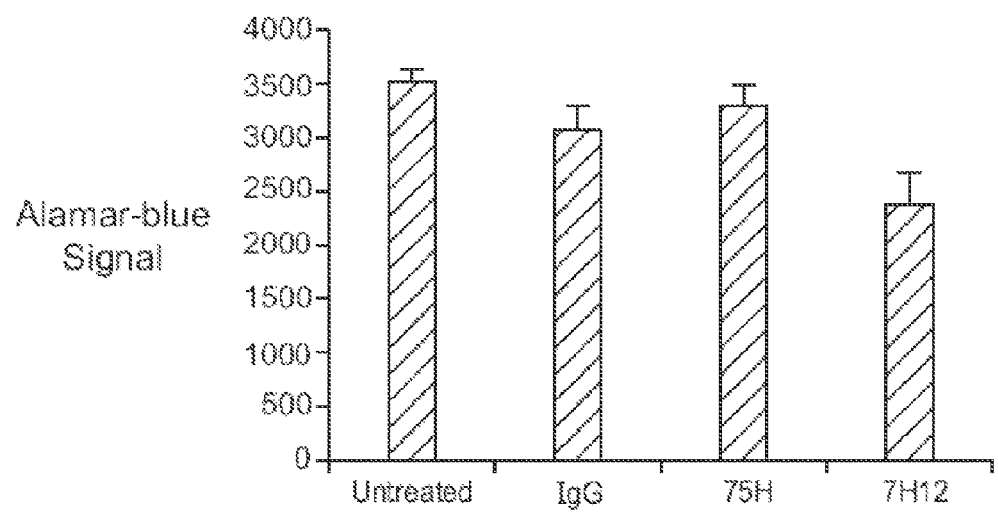

Cells are then labeled with BrdU by incubating them with 2 µl of BrdU stock solution (25 mg/ml in PBS) into 1 ml tissue culture medium (EGM2+all supplements from Clonetics (Cat #CC-4176). After this incubation cells were fixed with 4% PFA, treated with 1N HCl for 20 min, washed several times with PBS, and then blocked in 10% goat serum (PBS with 0.2% Triton) for 1-2 hours. Cells were then stained with a monoclonal antibody against BrdU (BD Cat #347580 1:40) PBS with 0.2% Triton and 5% goat serum) and incubated overnight at 4° C. Next day, the cells were washed 3 times with PBS and incubated with an Alexa-594-conjugated anti-rabbit (1:800) secondary antibody for 4 hours at room temperature in the dark. The wells are washed again and incubated with DAPI (1:10,000 in PBS) for 10 min. After a final wash with PBS, the total cell number per well was counted by taking a picture of the DAPI staining at 5×. Cells that were positive for BrdU in the same fields are photographed using the red filter. Proliferation is evaluated as the percentage of cells positive for BrdU in the field. The results were then analyzed using Excel. FIG. 5a shows the HUVEC total cell count at 32 hours after a starting cell number of 5000. FIG. 5b shows the HUVEC total cell count at 24 hours in antibody concentration 20 ug/ml.

Example 7

Migration Assay Protocol

Figure 7:
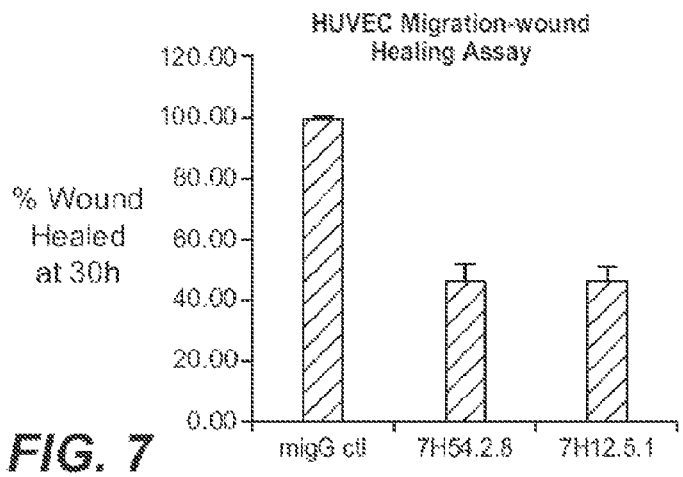
FIG. 7 is a bar graph quantitatively showing HUVEC cell migration after treatment with 7H5 and 7H12.

HUVEC cells were grown in EGM2+all supplements from Clonetics (Cat #CC-4176) on 5 µg/ml Fibronectin coated 24 well plates until confluency. Cells in the center of each well were then scared by a 2 µl pipette tip, and cells removed by the scarring were washed away. Cell culture medium with either control antibody, 7H5, or 7H12 were added to different wells. All tested antibodies were used at 20 µg/ml. Cells were then allowed to grow for 1 to 2 days. The wounded areas are monitored. FIG. 6 shows a photograph of HUVEC migration on 5 ug/ml fibronectin with 20 ug/ml anti-alpha5 antibodies (7H5) in ECM-2 at 0 hours and 30 hours. FIG. 7 is a graph of the % migration at 30 hours for cells treated with the 7H5 or 7H12 antibodies.

Example 8

HUVEC Activated-Caspase-3 Immunostaining Apoptosis Assays 96 well plates were coated with fibronectin (1 µg/ml) overnight. The plates were washed with PBS. Then, 3000-5000 HUVEC cells were plated per 96 well and grown overnight in complete medium (EBM-2 media (Cambrex CC-3156) with the EGM-2 SingleQuots (Cambrex CC-4176). If 2H-11 mouse endothelial cells will be use for the apoptosis assay, then the media is 50/50 media with 10% FBS.

The next day, one set of wells was changed to serum free media and incubated for 4-6 h to starve the cells and put them in a non-proliferating state. The other set of cells were kept in complete media and represented actively proliferating cells. After 4-6 hours, antibodies were added (including isotype controls). Generally, 3 wells are used for each condition. The cells were then incubated with the antibodies for 1-48 hours. Anti-integrin alpha5beta1 antibodies were generally tested at the following concentrations: 0 µg/ml, 4 µg/ml, 16 µg/ml, 60 µg/ml and 120 µg/ml.

Figure 8:
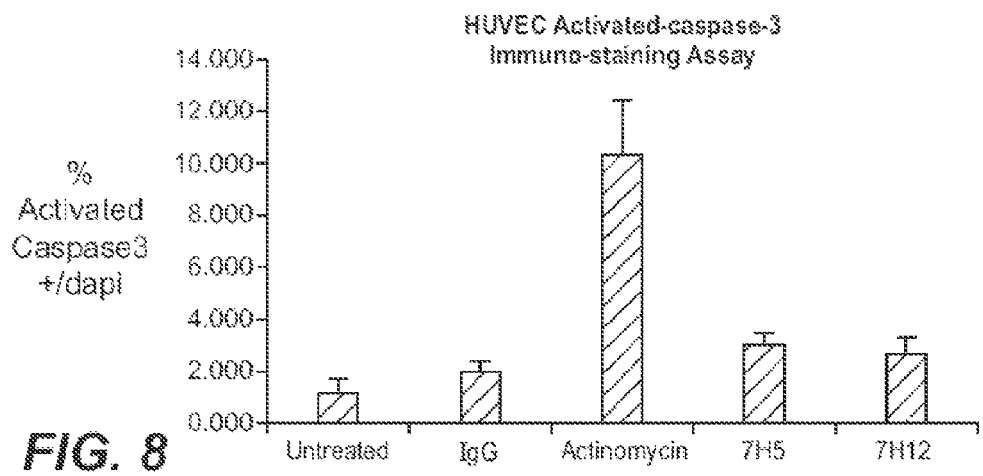
FIG. 8 is a bar graph showing the percentage of HUVEC cells expressing activated caspase-3 in an apoptosis assay after treatment with 7H5 and 7H12.

After this incubation, the cells were fixed with 4% PFA, blocked in 10% goat serum (PBS with 0.2% Triton) for 1-2 hours and then stained with a monoclonal antibody that specifically recognizes the activated form of Caspase 3 (e.g., rabbit anti-active Caspase-3 antibody from BioVision, 1:50 diluted in PBS with 0.2% Triton and 5% goat serum). The anti-caspase 3 antibody and fixed cells were incubated overnight at 4° C. The next day, the cells are washed 3 times with PBS and incubated with an Alexa-594-conjugated anti-rabbit (1:800) secondary antibody for 4 hours at room temperature in the dark. The wells were washed again and incubated with DAPI (1:10,000 in PBS) for 10 min. After a final wash with PBS, the total cell number per well is counted by taking a picture of the DAPI staining at 5×. Cells that are positive for activated caspasc3 in the same fields were photographed using the red filter. Apoptosis was evaluated as the percentage of cells positive for activated caspase-3. The results were then analyzed using Excel. FIG. 8 shows that 7H5 and 7H12 does not actively induce apoptosis.

Example 9

HUVEC Caspase-3/7 Activity Colometric Assay

Caspase 3/7 activity assay were conducted using the 7H5 and 7H12 antibodies (Apo-One Caspase-3/7 Assay from Promega, see Technical Bulletin No. 295 for a standard 96-well assay instructions).

Generally, 96 well plates were coated with fibronectin (1 µg/ml overnight. The plates were washed with PBS. Then, 3000-5000 HUVEC cells were plated per 96 well and grown overnight in complete medium (EBM-2 media (Cambrex CC-3156) with the EGM-2 SingleQuots (Cambrex CC-4176). If 2H-11 mouse endothelial cells are to be used for the apoptosis assay, then the media is 50/50 media with 10% FBS.

The next day, one set of wells was changed to serum free media and incubated for 4-6 h to starve the cells and put them in a non-proliferating state. The other set of cells were kept in complete media and represented actively proliferating cells. After 4-6 hours, antibodies were added (including isotype controls). Generally, 3 wells are used for each condition. The cells were then incubated with the antibodies for 24-48 hours. Anti-integrin alpha5beta1 antibodies were generally tested at the following concentrations: 0 µg/ml, 4 µg/ml, 16 µg/ml, 60 µg/ml and 120 µg/ml.

After this incubation 100 µl of the Apo-One Caspase 3/7 reagent was added to each well, and the plate was gently mixed using a plate shaker at 300 rpm for 30 seconds. The plate was then incubated at room temperature for 1 to 8 hours then using a plate reader. The fluorescence of each well at an excitation wavelength of 485 nm and an emission of 530 nm was measured.

Figure 9:
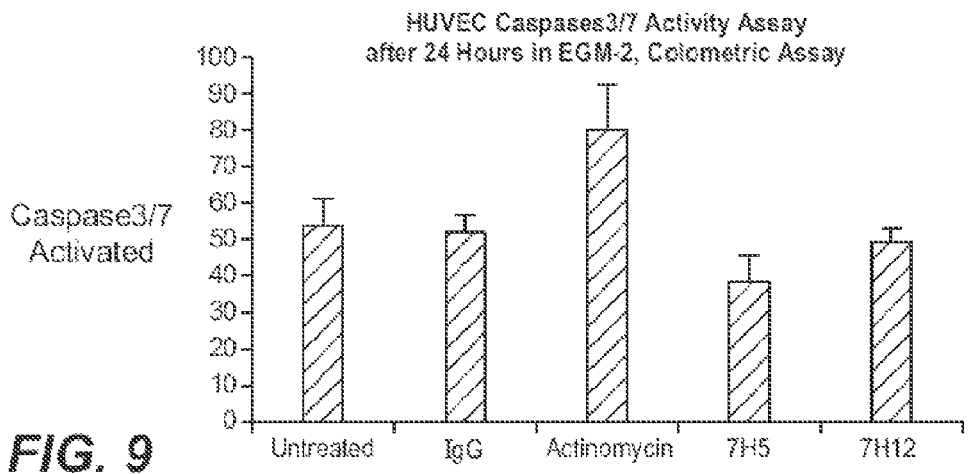
FIG. 9 is a bar graph showing HUVEC Caspase 3/7 activity after treatment with 7H5 and 7H12.

Fluorescent signal (RLU) resulting from the cleavage of the Caspase 3/7 substrate indicated apoptosis. FIG. 9 shows that 7H5 and 7H12 does not actively induce apoptosis.

Example 10

Tube Formation Assay

Anti-alpha5beta1 antibodies can be assessed for their ability to inhibit tube formation. The following is an example of a tube formation assay based on the HUVEC sprouting and tube formation assay described in Nakatsu et al. (2003) *Microvascular Research* 66 (2003) 102-112.

Generally, HUVEC cells can be mixed with detran-coated Cytodex 3 microcarriers (Amersham Pharmacia Biogech, Piscataway, N.J.) at a concentration of 400 HUVEC per bead In 1 ml of EGF-2 medium. Beads with cells can be shaken gently every 20 minutes for 4 hours at 37 C and 5% CO2. After incubating, the beads with cells can be transferred to a 25-cm2 tissue culture flask (BD Biosciences, Bedford, Mass.) and left for 12-16 H In 5 ml of EGM-2 at 37 C and 5% CO2. The following day, beads with cells can be washed three times with 1 ml of EGM-2 and resuspended at a concentration of 200 cell-coated beads/ml in 2.5 mg/ml of fibrinogen (Sigma, St. Louis, Mo.). Five hundred microliters of fibrinogen/bead solution can be added to 0.625 units of thrombin (Sigma) in one well of a 24 well tissue culture plate. The fibrinogen/bead solution can clot for 5 minutes at room temperature and then at 37 C and 5% CO2 for 20 minutes. One milliliter of EGM-2 (which contains 2% FBS) can be added to each well and equilibrated with the fibrin clot for 30 minutes at 37 C and 5% CO2. The media will be removed from the well and replaced with 1 ml of fresh media. Approximately, twenty thousand skin fibroblast cells (Detroit 551, ATCC, Rockville, Md.) can be plated on top of the clot. The media can be changed every other day. Bead assays can be monitored 7 days.

HUVEC-coated beads can be cultured in fibrin gels with or without 500 ul of anti-alpha5beta1 antibodies (7H5 and 7H12) on top of the gel for 2-3 days and then transferred to the stage of a Nicon Eclipse TE300, equipped with multidimensional axes and maintained at 37 C and 5% CO2 for 72 h. The final antibody concentration to be used can be calculated by taking into account the fibrin gel volume, i.e., final antibody concentration=total antibody weight/medium volume+fibrin gel volume. Images can be captured from multiple beads every 20 minutes using Metamorph software. Quantitation of vessels in vitro can be accomplished using a high-resolutions images of beads (e.g., IX70 Olympus microscope with a 4× objective). The number of sprouts per bead can be determined compared to a control (untreated), wherein sprout can be defined as a vessel of length equal to the diameter of the bead. Sprout length can be measured by arbitrary units.

Example 11

Combination Studies in Xenograft/Allograft Tumor Models

Concurrent and sequential administration of alpha5beta1 antagonist therapy and VEGF antagonist therapies can be evaluated in xenograft/allograft tumor models. Preferably, the models have little or no response to VEGF antagonist monotherapy. The following are examples of models that can be used: (a) Fo5 allograft in athymic nude mice (breast tumor derived from the mmtv-Her2 transgenic mice) (Finkle, D., et al., (2004) Clin. Cancer Res. 10:2499-2511); (b) HT29 xenograft in athymic nude mice (human colorectal line); and (c) RIP-TbAg (pancreatic tumors in a Tg model). The therapies can be administered typically intraperitoneally, subcutaneously or intravenously. For example, anti-VEGF antibody may be administered at 10 mg/kg once a week or 5 mg/kg twice a week. The amount of alpha5beta1 antagonist, such as an antibody, to be administered can be estimated based on its affinity and activity. In one experiment, the VEGF antagonist and the alpha5beta1 antagonist can be administered on a simultaneous schedule for 5-6 weeks. Alternatively or additionally, the VEGF antagonist and the alpha5beta1 antagonist can be administered on sequentially (e.g., anti-VEGF antibody for three weeks followed by dosing with anti-alpha5beta1 antibody for three weeks).

Treatment efficacy can be evaluated based on, among other things, tumor progression, tumor perfusion, tumor vascular density, morphology and/or survival. Tumor progression can be measured by e.g., tumor volume and/or tumor weights. FITC-lectin perfusion, as well as vascular marker staining can be used to evaluate vascular changes concomitant with neoplastic progression.

Example 12

MDA-MB231 Human Breast Tumor Model

HRLN female nude mice were injected with $5 \times 10^6$ MDA-MB231 human breast cancer cells subcutaneously in the flank. (HRLN is a strain name). Tumors were allowed to grow until they reached an average size of 80-120 cubic mm. Tumor bearing mice were then divided into 4 groups and treatment began when the average tumor volume per group was ~100 cubic mm.

Tumor volumes were measured twice a week during the study. Tumor volume measurement was carried out using a standard caliper measurement method. The hamster anti-mouse integrin alpha5 mab, known as 10E7, was generated at Genentech. The endpoint of the experiment was reached when the tumor was 1.5 gms or 60 days had passed, whichever came first. Responders may have been followed longer in some cases. Animals were euthanized when the endpoint was reached.

The treatment details are described below:
(1) Control group: anti ragweed control mab injected (10 mg/kg, interiperitoneally (ip), once a week)
(2) Anti-VEGF single agent group: anti-VEGF mab B20.4.1 injected (10 mg/kg, ip, once a week)
(3) Combination group: B20.41. (10 mg/kg, ip, once a week) plus hamster anti mouse integrin alpha5 mab 10E7 (10 mg/kg, ip, twice a week)
(4) Anti-integrin alpha5 single agent group: hamster anti-mouse integrin alpha5 mab 10E7 injected (10 mg/kg, ip, twice a week)

| | Control group data: | | | | | | | |
|---|---|---|---|---|---|---|---|---|
| | Day of Study | | | | | | | |
| | 1 | 4 | 9 | 13 | 16 | 20 | 23 | 27 |
| Animal ID | TV (mm3) | TV (mm3) | TV (mm3) | TV (mm3) | TV (mm3) | TV (mm3) | TV (mm3) | TV (mm3) |
| 1 | 63 | 75 | 196 | 405 | 550 | 486 | 600 | 1080 |
| 2 | 63 | 75 | 126 | 196 | 320 | 320 | 446 | 527 |
| 3 | 75 | 126 | 288 | 666 | 666 | 936 | 1080 | 2048 |
| 4 | 75 | 126 | 196 | 320 | 320 | 446 | 527 | 936 |
| 5 | 75 | 126 | 288 | 446 | 486 | 787 | 908 | 1764 |
| 6 | 88 | 144 | 221 | 288 | 288 | 405 | 550 | 550 |
| 7 | 88 | 144 | 320 | 550 | 726 | 1008 | 1352 | 2025 |
| 8 | 88 | 144 | 144 | 446 | 600 | 1268 | 1268 | 1913 |
| 9 | 108 | 144 | 245 | 486 | 650 | 700 | 908 | 1437 |
| 10 | 144 | 162 | 320 | 527 | 527 | 847 | 1352 | 2138 |

-continued

Control group data:

| | Day of Study | | | | | | | |
|---|---|---|---|---|---|---|---|---|
| Animal ID | 1 TV (mm3) | 4 TV (mm3) | 9 TV (mm3) | 13 TV (mm3) | 16 TV (mm3) | 20 TV (mm3) | 23 TV (mm3) | 27 TV (mm3) |
| Mean | 86.5 | 126.6 | 234.4 | 432.8 | 513.2 | 720.2 | 898.9 | 1441.6 |
| SEM | 7.7 | 9.3 | 22 | 43.5 | 49.7 | 96.6 | 112.3 | 198.2 |
| N | 10 | 10 | 10 | 10 | 10 | 10 | 10 | 10 |

Anti-VEGF single agent group data:

| | Day of Study | | | | | | | |
|---|---|---|---|---|---|---|---|---|
| Animal ID | 1 TV (mm3) | 4 TV (mm3) | 9 TV (mm3) | 13 TV (mm3) | 16 TV (mm3) | 20 TV (mm3) | 23 TV (mm3) | 27 TV (mm3) |
| 1 | 63 | 108 | 144 | 320 | 405 | 550 | 256 | 500 |
| 2 | 63 | 63 | 100 | 162 | 221 | 288 | 288 | 550 |
| 3 | 75 | 196 | 365 | 405 | 500 | 320 | 500 | 550 |
| 4 | 75 | 75 | 196 | 256 | 288 | 500 | 550 | 1099 |
| 5 | 75 | 126 | 196 | 320 | 500 | 500 | 550 | 787 |
| 6 | 88 | 144 | 221 | 320 | 352 | 446 | 446 | 600 |
| 7 | 88 | 196 | 365 | 405 | 405 | 666 | 726 | 864 |
| 8 | 88 | 196 | 288 | 320 | 352 | 384 | 288 | 365 |
| 9 | 108 | 172 | 256 | 500 | 405 | 320 | 288 | 320 |
| 10 | 144 | 245 | 416 | 567 | 750 | 968 | 1296 | 1296 |
| Mean | 86.5 | 152 | 254.6 | 357.5 | 417.8 | 494.1 | 518.8 | 693 |
| SEM | 7.7 | 18.7 | 32.6 | 36.9 | 45.8 | 64.5 | 99.1 | 100 |
| N | 10 | 10 | 10 | 10 | 10 | 10 | 10 | 10 |

Anti-VEGF and anti-Alpha5Beta1 data:

| | Day of Study | | | | | | | |
|---|---|---|---|---|---|---|---|---|
| Animal ID | 1 TV (mm3) | 4 TV (mm3) | 9 TV (mm3) | 13 TV (mm3) | 16 TV (mm3) | 20 TV (mm3) | 23 TV (mm3) | 27 TV (mm3) |
| 1 | 63 | 63 | 63 | 63 | 63 | 108 | 126 | 108 |
| 2 | 63 | 108 | 172 | 256 | 288 | 288 | 288 | 288 |
| 3 | 75 | 126 | 126 | 221 | 245 | 245 | 320 | 320 |
| 4 | 75 | 75 | 75 | 126 | 196 | 288 | 245 | 446 |
| 5 | 75 | 108 | 172 | 405 | 352 | 650 | 650 | 908 |
| 6 | 88 | 196 | 221 | 320 | 320 | 288 | 196 | 196 |
| 7 | 88 | 75 | 196 | 256 | 196 | 288 | 288 | 446 |
| 8 | 88 | 88 | 144 | 320 | 320 | 288 | 320 | 405 |
| 9 | 108 | 126 | 144 | 196 | 256 | 320 | 320 | 486 |
| 10 | 144 | 221 | 270 | 446 | 600 | 650 | 600 | 787 |
| Mean | 86.5 | 118.5 | 158.1 | 260.8 | 283.6 | 341.3 | 335.3 | 438.8 |
| SEM | 7.7 | 16.5 | 19.9 | 37.3 | 44 | 54.7 | 52.2 | 78.1 |
| N | 10 | 10 | 10 | 10 | 10 | 10 | 10 | 10 |

Anti-integrin alpha5 single agent group data:

| | Day of Study | | | | | | | |
|---|---|---|---|---|---|---|---|---|
| Animal ID | 1 TV (mm3) | 4 TV (mm3) | 9 TV (mm3) | 13 TV (mm3) | 16 TV (mm3) | 20 TV (mm3) | 23 TV (mm3) | 27 TV (mm3) |
| 1 | 63 | 75 | 196 | 320 | 486 | 787 | 1008 | 2025 |
| 2 | 63 | 108 | 126 | 365 | 365 | 726 | 1008 | 1352 |
| 3 | 75 | 75 | 144 | 288 | 288 | 550 | 600 | 1008 |

| | Anti-integrin alpha5 single agent group data: | | | | | | | |
|---|---|---|---|---|---|---|---|---|
| | Day of Study | | | | | | | |
| Animal ID | 1 TV (mm3) | 4 TV (mm3) | 9 TV (mm3) | 13 TV (mm3) | 16 TV (mm3) | 20 TV (mm3) | 23 TV (mm3) | 27 TV (mm3) |
| 4 | 75 | 108 | 144 | 320 | 320 | 847 | 1152 | 1960 |
| 5 | 75 | 108 | 172 | 365 | 365 | 550 | 486 | 1152 |
| 6 | 88 | 196 | 352 | 650 | 787 | 908 | 1352 | 1666 |
| 7 | 88 | 100 | 162 | 245 | 352 | 486 | 1764 | TP on Dec. 08, 2006 tumor exceeds 1500 mm3 |
| 8 | 88 | 126 | 162 | 320 | 446 | 486 | 650 | 650 |
| 9 | 108 | 288 | 446 | 600 | 1008 | 1352 | 936 | 3179 |
| 10 | 144 | 162 | 245 | 384 | 352 | 486 | 486 | 288 |
| Mean | 86.5 | 134.6 | 214.8 | 385.6 | 476.7 | 717.7 | 944.2 | 1475.6 |
| SEM | 7.7 | 20.7 | 33.1 | 42 | 74.2 | 86.7 | 129.7 | 286.4 |
| N | 10 | 10 | 10 | 10 | 10 | 10 | 10 | 9 |

This preliminary data shows early signs of anti-alpha5+anti-VEGF combinatorial activity.

Figure 11A:
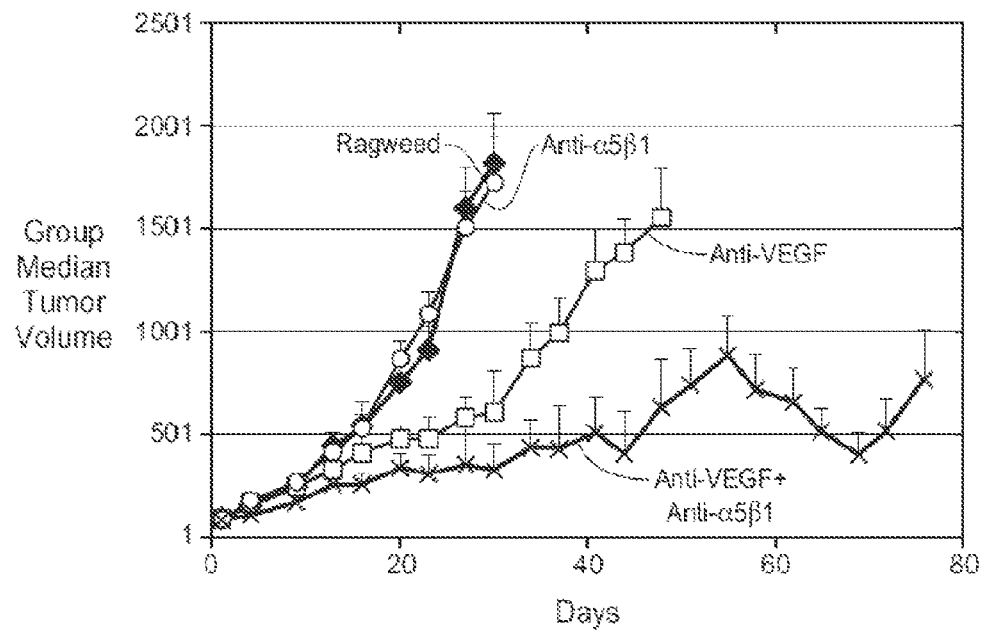
FIG. 11 shows the results of mice treated with anti-VEGF antibody+/−anti-alpha5beta1 antibody in a breast cancer model as (A) a graph showing the group median tumor volume of treated mice or (B) a Kaplan-Meier plot showing the percentage of animals remaining in the study as a function of time. Animals were removed from the study when their tumors reached or exceeded 1500 mm$^3$.
Figure 11B:
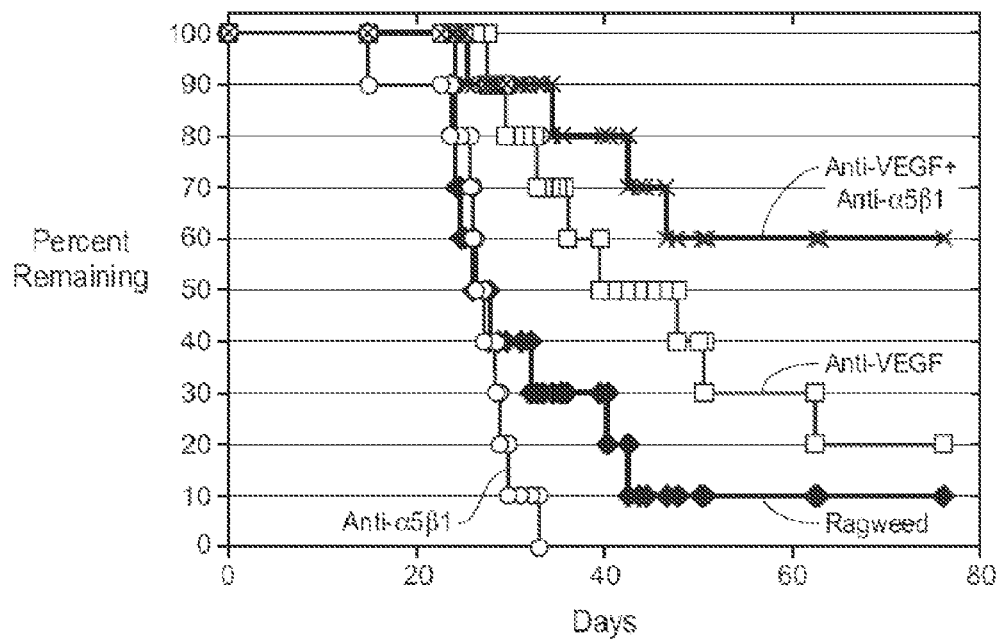

Following the endpoint of the study, the mean tumor volumes for each group were calculated (FIG. 11A). Kaplan-Meier plots were also constructed to show the percentage of animals remaining in the study as a function of time (FIG. 11B). The data shows that anti-integrin α5β1 antibody enhances the efficacy of anti-VEGF in a breast cancer model.

Example 13

7H12 and Bevacizumab in the Rabbit Ear Wound Healing Model

New Zealand White rabbits were weighed and anesthetized with isofluorane. In each rabbit, the hair was clipped from the inner surface and along the edges of both ear pinnae. Any remaining hair was removed from the surgical sites with depilatory lotion. The surgical sites were cleaned with beta-dine scrub followed by alcohol rinse. Using aseptic technique, a circular 8 mm punch biopsy instrument was used to produce one wound to the depth of the ear cartilage in each ear. The underlying perichondrium was removed with a periosteal elevator and a fine scissors. Opsite® adhesive bandage was placed over each wound, and the rabbit allowed to recover from anesthesia. Opsite® dressings were removed daily, wounds were inspected, treatments applied topically, and fresh dressing applied. Wound gap was calculated by measuring wound diameter on days 0 (immediately following surgery), 7, 10, 14, and 18.

Treatment groups were:
Bevacizumab (anti-VEGF antibody) 100 ug in 30 ul to each wound daily (n=4)

7H12 (anti-alpha5beta1 antibody) 100 ug in 30 ul to each wound daily (n=4)

Bevacizumab 100 ug in 15 ul+7H12 100 ug in 15 ul to each wound daily (n=4)

Trastuzumab (ant-HER2 antibody) 100 ug in 30 ul to each would daily (n=3)

Figure 10:
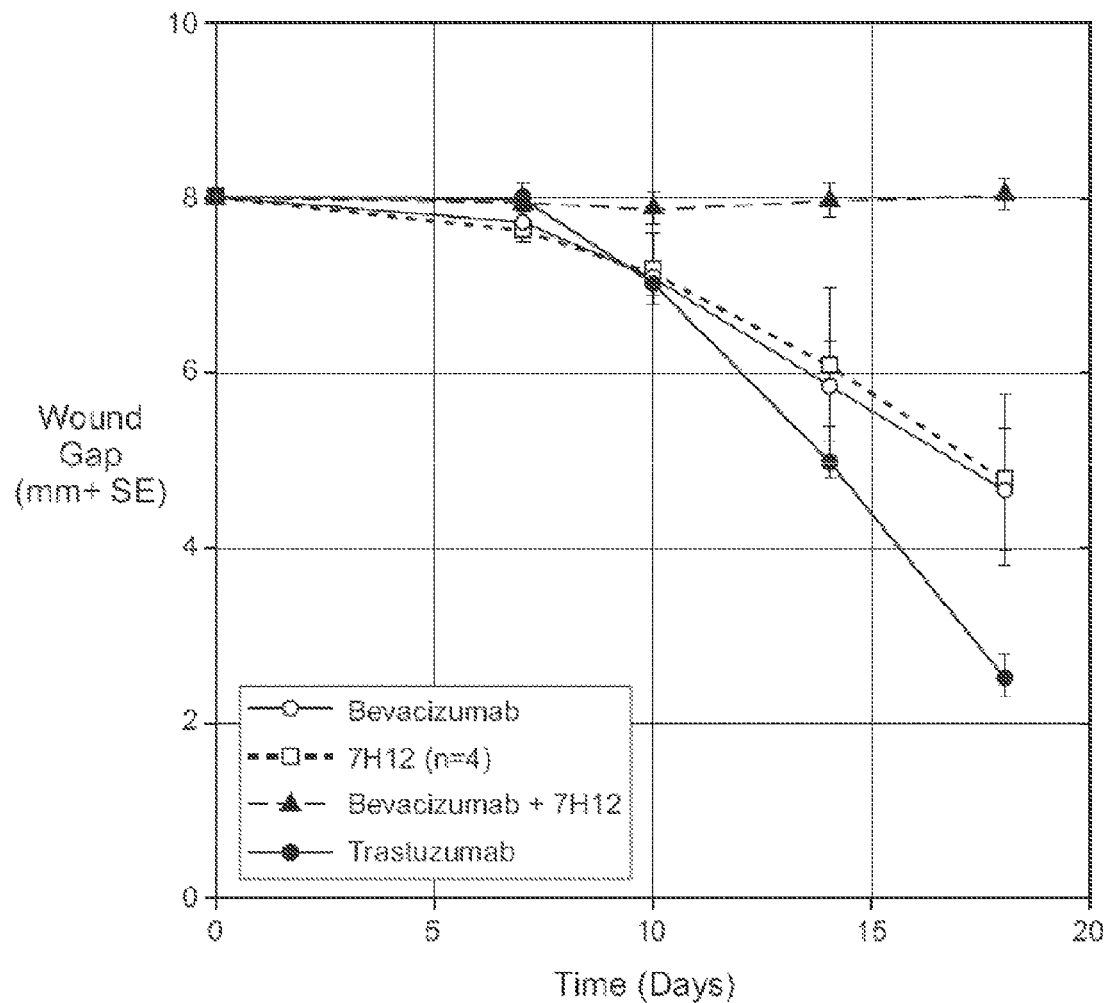
FIG. 10 is a graph showing 7H12 and/or Bevacizumab activity in a rabbit ear wound healing model.

The data shows that anti-VEGF and anti-alpha5beta1 combinatorial therapies have a striking effect in this angiogenesis model versus single agents alone (FIG. 10).

Example 14

Anti-Alpha5Beta1 and Anti-VEGF Combination Therapy in Colon Cancer

HRLN female nu/nu mice were injected with 1 mm3 HT29 tumor fragments (colon tumor) subcutaneously in their flanks. Tumors were allowed to grow until they reach an average size of 80-120 cubic mm before treatment with therapies. Tumor bearing mice were then divided into 4 groups:

| Group | # of mice | Treatment Regimen 1 | | | | Treatment Regimen 2 | | | |
|---|---|---|---|---|---|---|---|---|---|
| | | Agent | mg/kg | Route | Schedule | Agent | mg/kg | Route | Schedule |
| 1 | 10 | Control | 10 | IP | qwk x 7 | PBS | — | IP | biwk x 7 |
| 2 | 10 | B20-4.1 | 10 | IP | qwk x end | PBS | — | IP | 2x/wk to end |
| 3 | 10 | B20-4.1 | 10 | IP | qwk x end | 10E7 | 10 | IP | 2x/wk to end |
| 4 | 10 | PBS | — | IP | — | 10E7 | 10 | IP | 2x/wk to end |

Tumor volume measurement was carried out twice a week using a standard caliper measurement method. The hamster anti-mouse integrin alpha5 mab, known as 10E7, was generated at Genentech. The control IgG was an anti ragweed monoclonal antibody. Body weight was measured 5 times over 2 days then twice per week (biwk) to the end of the study. The endpoint of the experiment was a tumor volume of 1 gms or 90 days, whichever came first. Some responders were followed longer. When the endpoint was reached, the animals were euthanized. The dosing volume was 10 mL/kg (0.200 ml/20 g mouse), which volume was adjusted for body weight. For animals showing complete regression (CR), tissues at the site of tumor implantation were collected at endpoint and preserved in formulin followed by 70% EtOH for later study. All samples to be frozen were placed in a cryomold, wrapped in foil & snap frozen on liquid nitrogen.

Figure 12A:
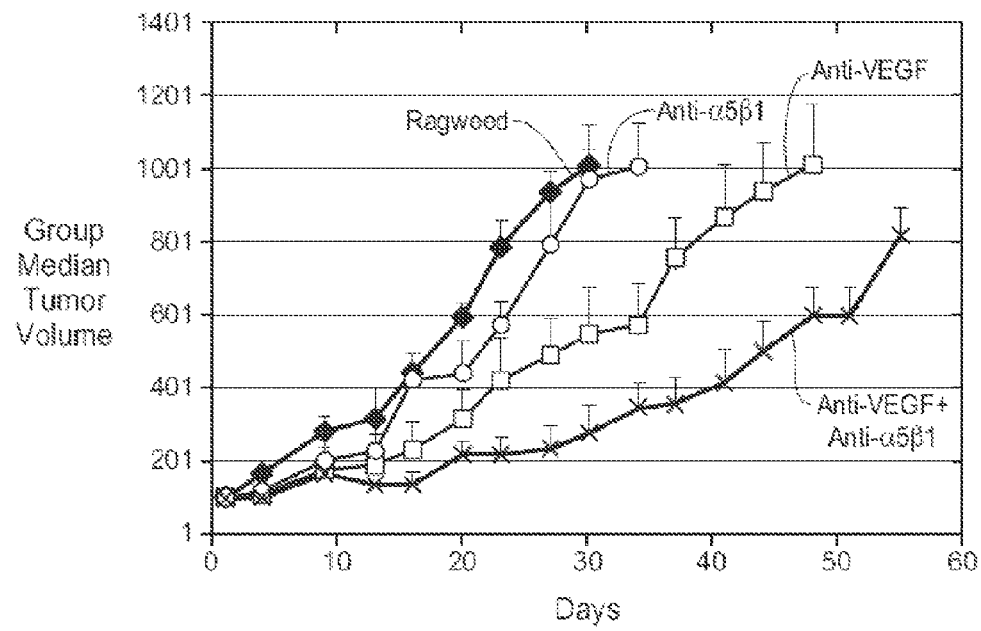
FIG. 12 shows the results of mice treated with anti-VEGF antibody+/−anti-alpha5beta1 antibody in a colon cancer model as (A) a graph showing the group median tumor volume of treated mice or (B) a Kaplan-Meier plot showing the percentage of animals remaining in the study as a function of time. Animals were removed from the study when their tumors reached or exceeded 1500 mm$^3$.
Figure 12B:
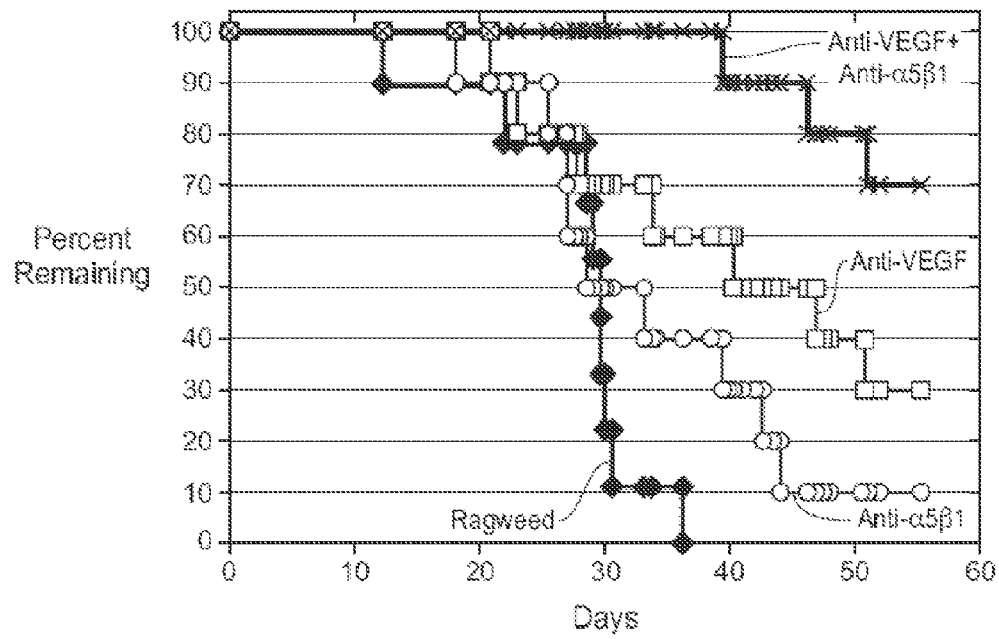

Following the endpoint of the study, the mean tumor volumes for each group were calculated (FIG. 12A). Kaplan-Meier plots were also constructed to show the percentage of animals remaining in the study as a function of time (FIG. 12B). The data shows that anti-integrin α5β1 antibody enhances the efficacy of anti-VEGF in a colon cancer model.

Example 15

Anti-Alpha5Beta1+Chemotherapy in a Colon Cancer

HRLN female nu/nu mice were injected with $5 \times 10^6$ HCT116 tumor cells (colon tumor cells) subcutaneously in their flanks. Tumors were allowed to grow until they reach an average size of 80-120 cubic mm before treatment with therapies. Tumor bearing mice were then divided into 4 groups:

| Group | # of mice | Treatment Regimen 1 | | | | Treatment Regimen 2 | | | |
|---|---|---|---|---|---|---|---|---|---|
| | | Agent | mg/kg | Route | Schedule | Agent | mg/kg | Route | Schedule |
| 1 | 10 | PBS | — | IP | biwk x 7 | — | — | IP | — |
| 2 | 10 | 10E7 | 10 | IP | biwk x 7 | — | — | IP | — |
| 3 | 10 | PBS | — | IP | biwk x 7 | irinotecan | 100 | IP | qwk x 3 |
| 4 | 10 | 10E7 | 10 | IP | biwk x 7 | irinotecan | 100 | IP | qwk x 3 |

Tumor volume measurement was carried out twice a week using a standard caliper measurement method. The hamster anti-mouse integrin alpha5 mab, known as 10E7, was generated at Genentech. Body weight was measured 5 times over 2 days then twice per week (biwk) to the end of the study. The endpoint of the experiment was a tumor volume of 1.5 gms or 60 days, whichever came first. Some responders were followed longer. When the endpoint was reached, the animals were euthanized. The dosing volume was 10 mL/kg (0.200 ml/20 g mouse), which volume was adjusted for body weight. 10E7 was administered 30 minutes before irinotecan administration. For animals showing complete regression (CR), tissues at the site of tumor implantation were collected at endpoint and preserved in formulin followed by 70% EtOH for later study. All samples to be frozen were placed in a cryomold, wrapped in foil & snap frozen on liquid nitrogen.

Figure 13A:
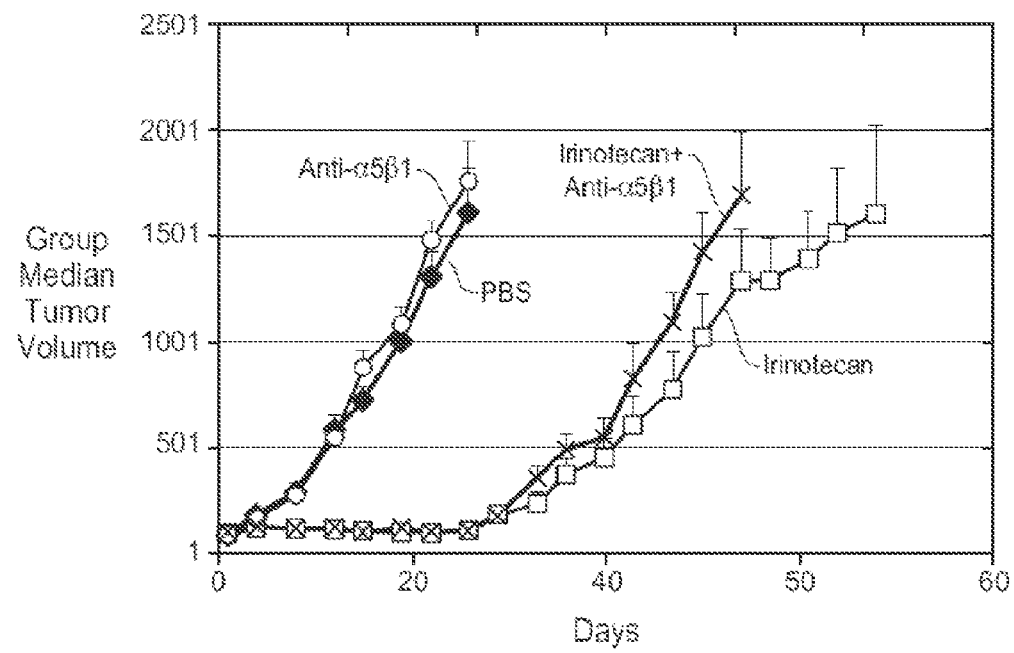
FIG. 13 shows the results of mice treated with anti-alpha5beta1 antibody or a chemotherapeutic agent in a colon cancer model as (A) a graph showing the group median tumor volume of treated mice or (B) a Kaplan-Meier plot showing the percentage of animals remaining in the study as a function of time. Animals were removed from the study when their tumors reached or exceeded 1500 mm$^3$.
Figure 13B:
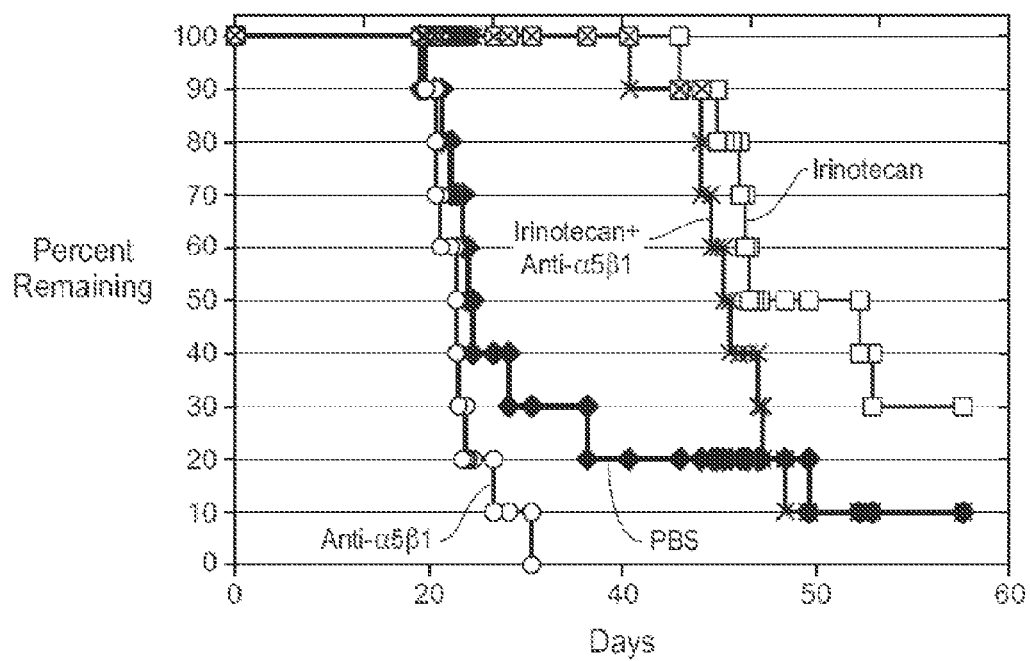

Following the endpoint of the study, the mean tumor volumes for each group were calculated (FIG. 13A). Kaplan-Meier plots were also constructed to show the percentage of animals remaining in the study as a function of time (FIG. 13B). The data shows that an anti-integrin alpha5beta1 antibody does not enhance the efficacy the activity of a chemotherapeutic agent (irinotecan) in a colon cancer model, but also it does not hinder the activity of the chemotherapeutic agent. This observation is consistent with our belief that vascular damage should occur before anti-alpha5beta1 therapy can be significantly useful in anti-angiogenesis, in general, and in particular anti-angiogenesis in an oncological setting. Such vascular damage can be caused by a VEGF antagonist, such as the AVASTIN® antibody. By itself, the chemotherapeutic agent in this model did not cause significant vascular damage. One could envision the use of all of these agents (VEGF antagonist/alpha5beta1 antagonist/chemotherapeutic agent) simultaneously or sequentially, so that an VEGF antagonist is present to cause vascular damage.

Example 16

Alpha5Beta1 Scatchard Plots

The anti-alpha5beta1 antibodies were iodinated using the Iodogen method, and radiolabelled antibody was purified from free $^{125}$I—Na by gel filtration using a PD-10 column. R9ab cells, a rabbit fibroblast cell line (purchased from ATCC, No. CCL-193) were seeded at ~50,000 per well in 24 well plates and incubated for 48 hr in 5% CO2 at 37° C. The cells were washed three times with binding buffer (50:50 DMEM/F12 media containing 2% FBS and 50 mM HEPES, pH7.2) and then incubated on ice for 15 minutes. The washed cells were incubated for 4 hours on ice with approximately 50 pM of $^{125}$I-anti-alpha5beta1 monoclonal antibody containing decreasing concentrations of unlabeled anti-alpha5beta1 monoclonal antibody serially diluted from 0.5 uM in binding buffer for 13 concentrations assayed in triplicate. The cells were washed three times with binding buffer and then solubilized with 200 ul of SDS lysis buffer (1% SDS, 8M urea, 100 mM glycine, pH 3.0). The cell lysates were counted on a Wallac Wizard 1470 gamma counter. The binding data was evaluated using Genentech's program NewLigand, which uses the curve fitting algorithm of Munson and Robard (Munson, P. and Robard, D. (1980) Anal. Biochem. 107: 220-239) to determine the binding affinity of the antibody and concentration of binding sites. FIGS. 14 and 15 show that the 7H5 antibody has a Kd of 0.10 nM and the 7H12 antibody has a Kd of 0.30 nM, respectively, in these binding assays.

Example 17

Anti-Integrin Alpha5Beta1 IgG Epitope Mapping/Competitive Binding Assays

Three-fold serial dilutions of anti-integrin α5β1 IgGs were first incubated with 96-well Nunc Maxisorp plate coated human integrin α5β1 antigen (1 ug/ml; R&D) in PBST buffer (PBS and 0.5% (w/v) BSA and 0.05% (v/v) Tween20) for 1-2 hr at room temperature, following by adding 0.3 nM biotinylated h7H5.v1 hIgG1 (an antibody variant of 7H5 generated by Genentech, Inc.), which was determined first by sub-maximal binding signal (50-70%), for 15 minutes. Then the plate was washed with PBT buffer (PBS and 0.05% (v/v) Tween20)

for 5 times. The bound biotinylated h7H5.v1 hIgG1 detected with streptavidin horseradish peroxidase conjugate (Pierce) diluted 1:2500 in PBST buffer, developed with 3,3',5,5'-tetramethylbenzidine (TMB, Kirkegaard & Perry Labs, Gaithersburg, Md.) substrate for approximately 5 min, quenched with 1.0 M $H_3PO_4$, and read spectrophotometrically at 450 nm. The curves were fit with a four-parameter non-linear regression curve-fitting program (Kaleidagraph, Synergy Software).

Figure 16:
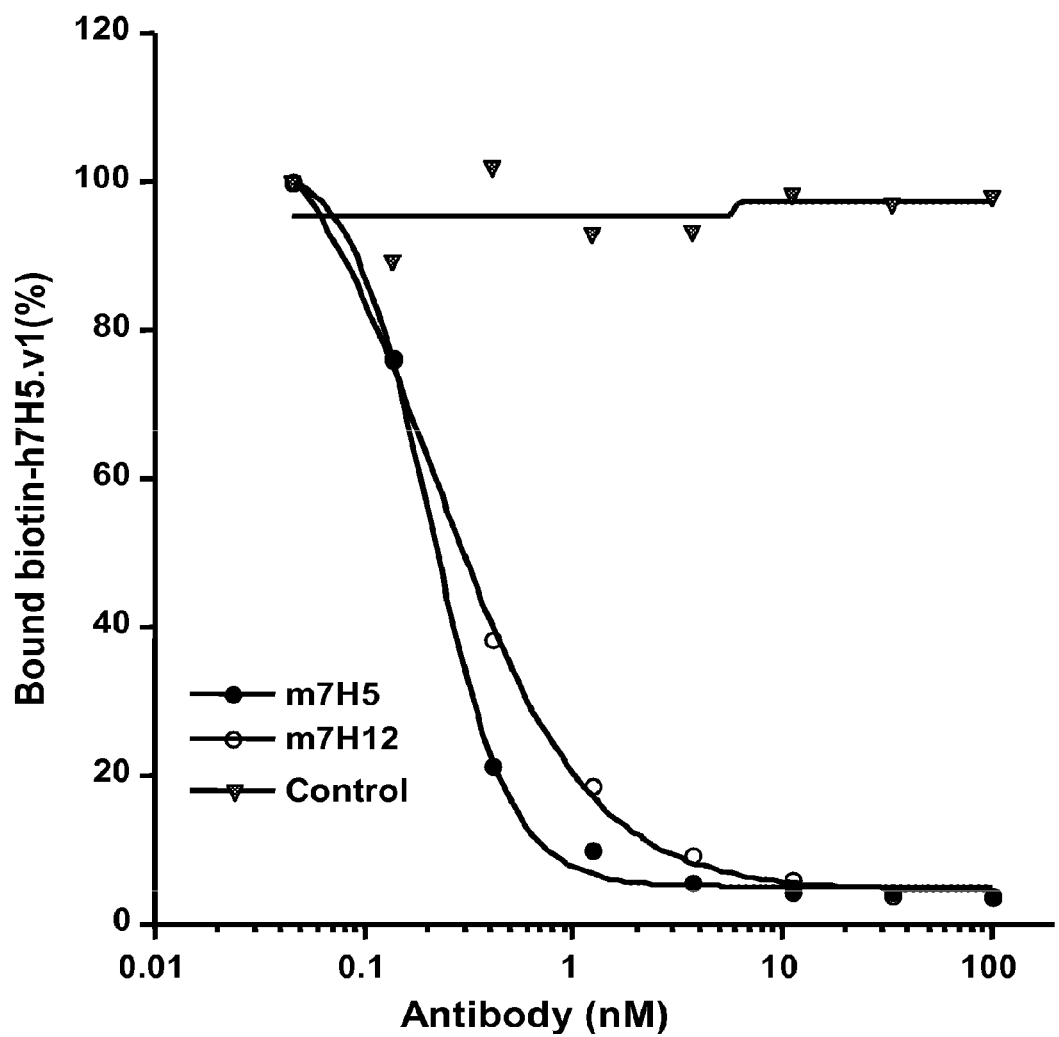
FIG. 16 shows the results of anti-Integrin alpha5beta1 IgG epitope mapping/competitive binding assays with various anti-alpha5beta1 antibodies.

FIG. 16 shows that bound h7H5.v1 was competed by increasing amounts of cold m7H5. In fact, the m7H5 competition curve was nearly identical to the h7H5.v1 competition curve (data not shown). Cold m7H12 also competed with biotin-h7H5.v1 for binding to alpha5beta1, indicating that the h7H5.v1 and m7H12 binding epitopes on alpha5beta1 are overlapping. The control antibody, on the other hand, did not compete with bound h7H5.v1.

The invention claimed is:

1. An antibody that can bind human alpha5beta1 and competitively inhibit the binding of an anti-alpha5beta1 antibody to human alpha5beta1, wherein the anti-alpha5beta1 antibody is produced by a hybridoma selected from the group consisting of the hybridoma deposited as Alpha5/beta1 7H5.4.2.8 (ATCC No. PTA-7421) and the hybridoma deposited as Alpha5/beta1 7H12.5.1.4 (ATCC No. PTA-7420) in the ATCC on Mar. 7, 2006.

2. The antibody of claim 1, wherein the antibody comprises at least one hypervariable region substantially corresponding to a hypervariable region of the anti-alpha5beta1 antibody that is produced by a hybridoma selected from the group consisting of the hybridoma deposited as Alpha5/beta1 7H5.4.2.8 (ATCC No. PTA-7421) and the hybridoma deposited as Alpha5/beta1 7H12.5.1.4 (ATCC No. PTA-7420) in the ATCC on Mar. 7, 2006.

3. The antibody of claim 1, wherein the antibody comprises a variable domain comprising CDRs substantially corresponding to the CDRs of the anti-alpha5beta1 antibody that is produced by a hybridoma selected from the group consisting of the hybridoma deposited as Alpha5/beta1 7H5.4.2.8 (ATCC No. PTA-7421) and the hybridoma deposited as Alpha5/beta1 7H12.5.1.4 (ATCC No. PTA-7420) in the ATCC on Mar. 7, 2006.

4. The antibody of claim 3, wherein the antibody is produced by a hybridoma selected from the group consisting of the hybridoma deposited as Alpha5/beta1 7H5.4.2.8 (ATCC No. PTA-7421) and the hyridoma deposited as Alpha5/beta1 7H12.5.1.4 (ATCC No. PTA-7420) in the ATCC on Mar. 7, 2006.

5. The antibody of claim 3, wherein the antibody is a humanized or chimeric antibody.

6. The antibody of claim 3, wherein the antibody binds a human alpha5beta1 or alpha5 with a Kd between 500 nM and 1 pM.

7. The antibody of claim 3, wherein the antibody comprises a Fc sequence of a human IgG.

8. The antibody of claim 3, wherein the human IgG is IgG1 or IgG4.

9. The antibody of claim 3, wherein the antibody comprises a Fc sequence that lacks antibody dependent cellular cytotoxicity (ADCC) effector function.

10. The antibody of claim 3, wherein the antibody is selected from the group consisting of a Fab, Fab', a F(ab)'$_2$, single-chain Fv (scFv), an Fv fragment; a diabody and a linear antibody.

11. The antibody of claim 3, wherein the antibody is a multi-specific antibody.

12. The antibody of claim 3 conjugated to a therapeutic agent.

13. The antibody of claim 12, wherein the therapeutic agent is selected from the group consisting of a cytotoxic agent, a radioisotope and a chemotherapeutic agent.

14. The antibody of claim 3 conjugated to a label.

15. The antibody of claim 14, wherein the label is selected from the group consisting of a radioisotope, fluorescent dye and enzyme.

16. The antibody of claim 1, wherein the antibody comprises a heavy chain variable domain comprising the three CDRs and a light chain variable domain comprising the three CDRs, wherein the six CDRs correspond to the CDRs in the anti-alpha5beta1 antibody produced by a hybridoma that is selected from the group consisting of the hybridoma deposited as Alpha5/beta1 7H5.4.2.8 (ATCC No. PTA-7421) and the hybridoma deposited as Alpha5/beta1 7H12.5.1.4 (ATCC No. PTA-7420) in the ATCC on Mar. 7, 2006.

17. The antibody of claim 1, wherein the antibody comprises a heavy chain variable domain comprising the three hypervariable regions and a light chain variable domain comprising the three hypervariable regions, wherein the six hypervariable regions correspond to the hypervariable regions in the anti-alpha5beta1 antibody produced by a hybridoma that is selected from the group consisting of the hybridoma deposited as Alpha5/beta1 7H5.4.2.8 (ATCC No. PTA-7421) and the hybridoma deposited as Alpha5/beta1 7H12.5.1.4 (ATCC No. PTA-7420) in the ATCC on Mar. 7, 2006.

18. The antibody of claim 1, wherein the antibody comprises the heavy chain variable domain sequence and the light chain variable domain sequence of the antibody produced by the hybridoma deposited as Alpha5/beta1 7H5.4.2.8 (ATCC No. PTA-7421) in the ATCC on Mar. 7, 2006.

19. The antibody of claim 1, wherein the antibody comprises the heavy chain variable domain sequence and the light chain variable domain sequence of the antibody produced by the hybridoma deposited as Alpha5/beta1 7H12.5.1.4 (ATCC No. PTA-7420) in the ATCC on Mar. 7, 2006.

20. A composition comprising the antibody of claim 1 and a pharmaceutically acceptable carrier.

21. A kit for detecting human alpha5beta1 in a subject comprising the antibody of claim 1 and instructions for using the antibody for detecting human alpha5beta1.

22. The kit of claim 21, wherein the subject has been treated with a VEGF antagonist.

* * * * *

```
                           SEQUENCE LISTING

<160> NUMBER OF SEQ ID NOS: 5

<210> SEQ ID NO 1
<211> LENGTH: 124
<212> TYPE: PRT
<213> ORGANISM: Mus musculus

<400> SEQUENCE: 1

Gln Val Gln Leu Lys Glu Ser Gly Pro Gly Leu Val Ala Pro Ser
  1               5                  10                  15

Gln Ser Leu Ser Ile Thr Cys Thr Ile Ser Gly Phe Ser Leu Thr
                 20                  25                  30

Asp Tyr Gly Val His Trp Val Arg Gln Pro Pro Gly Lys Gly Leu
                 35                  40                  45

Glu Trp Leu Val Val Ile Trp Ser Asp Gly Ser Ser Thr Tyr Asn
                 50                  55                  60

Ser Ala Leu Lys Ser Arg Met Thr Ile Arg Lys Asp Asn Ser Lys
                 65                  70                  75

Ser Gln Val Phe Leu Ile Met Asn Ser Leu Gln Thr Asp Asp Ser
                 80                  85                  90

Ala Met Tyr Tyr Cys Ala Arg His Gly Thr Tyr Tyr Gly Met Thr
                 95                 100                 105

Thr Thr Gly Asp Ala Leu Asp Tyr Trp Gly Gln Gly Thr Ser Val
                110                 115                 120

Thr Val Ser Ser

<210> SEQ ID NO 2
<211> LENGTH: 108
<212> TYPE: PRT
<213> ORGANISM: Mus musculus

<400> SEQUENCE: 2

Gln Ile Val Leu Thr Gln Ser Pro Ala Ile Met Ser Ala Ser Leu
  1               5                  10                  15

Gly Glu Arg Val Thr Met Thr Cys Thr Ala Ser Ser Ser Val Ser
                 20                  25                  30

Ser Asn Tyr Leu His Trp Tyr Gln Gln Lys Pro Gly Ser Ala Pro
                 35                  40                  45

Asn Leu Trp Ile Tyr Ser Thr Ser Asn Leu Ala Ser Gly Val Pro
                 50                  55                  60

Ala Arg Phe Ser Gly Ser Gly Ser Gly Thr Ser Tyr Ser Leu Thr
                 65                  70                  75

Ile Ser Ser Met Glu Ala Glu Asp Ala Ala Thr Tyr Tyr Cys His
                 80                  85                  90

Gln Tyr Leu Arg Ser Pro Pro Thr Phe Gly Gly Gly Thr Lys Leu
                 95                 100                 105
```

Glu Ile Lys

<210> SEQ ID NO 3
<211> LENGTH: 451
<212> TYPE: PRT
<213> ORGANISM: Artificial sequence
<220> FEATURE:
<223> OTHER INFORMATION: Synthetic Polypeptide

<400> SEQUENCE: 3

```
Gln Val Gln Leu Lys Glu Ser Gly Pro Gly Leu Val Ala Pro Ser
 1               5                  10                  15

Gln Ser Leu Ser Ile Thr Cys Thr Ile Ser Gly Phe Ser Leu Thr
                20                  25                  30

Asp Tyr Gly Val His Trp Val Arg Gln Pro Pro Gly Lys Gly Leu
                35                  40                  45

Glu Trp Leu Val Val Ile Trp Ser Asp Gly Ser Ser Thr Tyr Asn
                50                  55                  60

Ser Ala Leu Lys Ser Arg Met Thr Ile Arg Lys Asp Asn Ser Lys
                65                  70                  75

Ser Gln Val Phe Leu Ile Met Asn Ser Leu Gln Thr Asp Asp Ser
                80                  85                  90

Ala Met Tyr Tyr Cys Ala Arg His Gly Thr Tyr Tyr Gly Met Thr
                95                 100                 105

Thr Thr Gly Asp Ala Leu Asp Tyr Trp Gly Gln Gly Thr Ser Val
               110                 115                 120

Thr Val Ser Ser Ala Ser Thr Lys Gly Pro Ser Val Phe Pro Leu
               125                 130                 135

Ala Pro Cys Ser Arg Ser Thr Ser Glu Ser Thr Ala Ala Leu Gly
               140                 145                 150

Cys Leu Val Lys Asp Tyr Phe Pro Glu Pro Val Thr Val Ser Trp
               155                 160                 165

Asn Ser Gly Ala Leu Thr Ser Gly Val His Thr Phe Pro Ala Val
               170                 175                 180

Leu Gln Ser Ser Gly Leu Tyr Ser Leu Ser Ser Val Val Thr Val
               185                 190                 195

Pro Ser Ser Ser Leu Gly Thr Lys Thr Tyr Thr Cys Asn Val Asp
               200                 205                 210

His Lys Pro Ser Asn Thr Lys Val Asp Lys Arg Val Glu Ser Lys
               215                 220                 225

Tyr Gly Pro Pro Cys Pro Ser Cys Pro Ala Pro Glu Phe Leu Gly
               230                 235                 240

Gly Pro Ser Val Phe Leu Phe Pro Pro Lys Pro Lys Asp Thr Leu
               245                 250                 255

Met Ile Ser Arg Thr Pro Glu Val Thr Cys Val Val Val Asp Val
               260                 265                 270

Ser Gln Glu Asp Pro Glu Val Gln Phe Asn Trp Tyr Val Asp Gly
               275                 280                 285

Val Glu Val His Asn Ala Lys Thr Lys Pro Arg Glu Glu Gln Phe
               290                 295                 300

Asn Ser Thr Tyr Arg Val Val Ser Val Leu Thr Val Leu His Gln
               305                 310                 315

Asp Trp Leu Asn Gly Lys Glu Tyr Lys Cys Lys Val Ser Asn Lys
               320                 325                 330

Gly Leu Pro Ser Ser Ile Glu Lys Thr Ile Ser Lys Ala Lys Gly
               335                 340                 345
```

-continued

```
Gln Pro Arg Glu Pro Gln Val Tyr Thr Leu Pro Pro Ser Gln Glu
            350                 355                 360

Glu Met Thr Lys Asn Gln Val Ser Leu Thr Cys Leu Val Lys Gly
            365                 370                 375

Phe Tyr Pro Ser Asp Ile Ala Val Glu Trp Glu Ser Asn Gly Gln
            380                 385                 390

Pro Glu Asn Asn Tyr Lys Thr Thr Pro Pro Val Leu Asp Ser Asp
            395                 400                 405

Gly Ser Phe Phe Leu Tyr Ser Arg Leu Thr Val Asp Lys Ser Arg
            410                 415                 420

Trp Gln Glu Gly Asn Val Phe Ser Cys Ser Val Met His Glu Ala
            425                 430                 435

Leu His Asn His Tyr Thr Gln Lys Ser Leu Ser Leu Ser Leu Gly
            440                 445                 450

Lys

<210> SEQ ID NO 4
<211> LENGTH: 215
<212> TYPE: PRT
<213> ORGANISM: Artificial sequence
<220> FEATURE:
<223> OTHER INFORMATION: Synthetic Polypeptide

<400> SEQUENCE: 4

Gln Ile Val Leu Thr Gln Ser Pro Ala Ile Met Ser Ala Ser Leu
  1               5                  10                  15

Gly Glu Arg Val Thr Met Thr Cys Thr Ala Ser Ser Ser Val Ser
             20                  25                  30

Ser Asn Tyr Leu His Trp Tyr Gln Gln Lys Pro Gly Ser Ala Pro
             35                  40                  45

Asn Leu Trp Ile Tyr Ser Thr Ser Asn Leu Ala Ser Gly Val Pro
             50                  55                  60

Ala Arg Phe Ser Gly Ser Gly Ser Gly Thr Ser Tyr Ser Leu Thr
             65                  70                  75

Ile Ser Ser Met Glu Ala Glu Asp Ala Ala Thr Tyr Tyr Cys His
             80                  85                  90

Gln Tyr Leu Arg Ser Pro Pro Thr Phe Gly Gly Gly Thr Lys Leu
             95                 100                 105

Glu Ile Lys Arg Thr Val Ala Ala Pro Ser Val Phe Ile Phe Pro
            110                 115                 120

Pro Ser Asp Glu Gln Leu Lys Ser Gly Thr Ala Ser Val Val Cys
            125                 130                 135

Leu Leu Asn Asn Phe Tyr Pro Arg Glu Ala Lys Val Gln Trp Lys
            140                 145                 150

Val Asp Asn Ala Leu Gln Ser Gly Asn Ser Gln Glu Ser Val Thr
            155                 160                 165

Glu Gln Asp Ser Lys Asp Ser Thr Tyr Ser Leu Ser Ser Thr Leu
            170                 175                 180

Thr Leu Ser Lys Ala Asp Tyr Glu Lys His Lys Val Tyr Ala Cys
            185                 190                 195

Glu Val Thr His Gln Gly Leu Ser Ser Pro Val Thr Lys Ser Phe
            200                 205                 210

Asn Arg Gly Glu Cys
            215
```

-continued

```
<210> SEQ ID NO 5
<211> LENGTH: 232
<212> TYPE: PRT
<213> ORGANISM: Artificial sequence
<220> FEATURE:
<223> OTHER INFORMATION: Synthetic Polypeptide

<400> SEQUENCE: 5

Gln Val Gln Leu Lys Glu Ser Gly Pro Gly Leu Val Ala Pro Ser
  1               5                  10                  15

Gln Ser Leu Ser Ile Thr Cys Thr Ile Ser Gly Phe Ser Leu Thr
             20                  25                  30

Asp Tyr Gly Val His Trp Val Arg Gln Pro Pro Gly Lys Gly Leu
             35                  40                  45

Glu Trp Leu Val Val Ile Trp Ser Asp Gly Ser Ser Thr Tyr Asn
             50                  55                  60

Ser Ala Leu Lys Ser Arg Met Thr Ile Arg Lys Asp Asn Ser Lys
 65                  70                  75

Ser Gln Val Phe Leu Ile Met Asn Ser Leu Gln Thr Asp Asp Ser
             80                  85                  90

Ala Met Tyr Tyr Cys Ala Arg His Gly Thr Tyr Tyr Gly Met Thr
             95                 100                 105

Thr Thr Gly Asp Ala Leu Asp Tyr Trp Gly Gln Gly Thr Ser Val
                110                 115                 120

Thr Val Ser Ser Ala Ser Thr Lys Gly Pro Ser Val Phe Pro Leu
                125                 130                 135

Ala Pro Cys Ser Arg Ser Thr Ser Glu Ser Thr Ala Ala Leu Gly
                140                 145                 150

Cys Leu Val Lys Asp Tyr Phe Pro Glu Pro Val Thr Val Ser Trp
                155                 160                 165

Asn Ser Gly Ala Leu Thr Ser Gly Val His Thr Phe Pro Ala Val
                170                 175                 180

Leu Gln Ser Ser Gly Leu Tyr Ser Leu Ser Ser Val Val Thr Val
                185                 190                 195

Pro Ser Ser Ser Leu Gly Thr Lys Thr Tyr Thr Cys Asn Val Asp
                200                 205                 210

His Lys Pro Ser Asn Thr Lys Val Asp Lys Arg Val Glu Ser Lys
                215                 220                 225

Tyr Gly Pro Pro Cys Pro Ser
                230
```